United States Patent
McGee Perkins et al.

(10) Patent No.: US 8,991,391 B2
(45) Date of Patent: Mar. 31, 2015

(54) DRY POWDER INHALERS WITH ENDLESS STRIPS AND COOPERATING PIERCERS AND RELATED METHODS

(75) Inventors: George McGee Perkins, Cambridge (GB); Scott Alexander Lewis, Cambridge (GB); Andrew Murray Gow, Cambridge (GB); David Harris, Cambridge (GB)

(73) Assignee: Oriel Therapeutics, Inc., Durham, NC (US)

( * ) Notice: Subject to any disclaimer, the term of this patent is extended or adjusted under 35 U.S.C. 154(b) by 1036 days.

(21) Appl. No.: 13/063,511

(22) PCT Filed: Sep. 25, 2009

(86) PCT No.: PCT/US2009/005335
§ 371 (c)(1),
(2), (4) Date: Jun. 3, 2011

(87) PCT Pub. No.: WO2010/039200
PCT Pub. Date: Apr. 8, 2010

(65) Prior Publication Data
US 2011/0226244 A1   Sep. 22, 2011

Related U.S. Application Data

(60) Provisional application No. 61/101,175, filed on Sep. 30, 2008.

(51) Int. Cl.
*A61M 15/00* (2006.01)
*A61M 16/00* (2006.01)
*B05D 7/14* (2006.01)
*B65D 83/06* (2006.01)

(52) U.S. Cl.
CPC ....... *A61M 15/0045* (2013.01); *A61M 15/0035* (2013.01); *A61M 15/0051* (2013.01)
USPC .................................. 128/203.21; 128/203.15

(58) Field of Classification Search
CPC .......... A61F 5/08; A61M 16/00; A61M 16/18; A61M 2202/064; A61M 15/0028
USPC ........ 222/94, 81–83, 105, 183; 206/389, 531; 128/200.24, 203.12, 203.15, 203.21
See application file for complete search history.

(56) References Cited

U.S. PATENT DOCUMENTS 5,415,162 A  5/1995 Casper
5,857,457 A  1/1999 Hyppola (Continued)

OTHER PUBLICATIONS

International Search Report and Written Opinion for corresponding PCT Application No. PCT/US2009/005335, date of mailing Mar. 30, 2010.

*Primary Examiner* — Tan-Uyen (Jackie) T Ho
*Assistant Examiner* — Mark Wardas
(74) *Attorney, Agent, or Firm* — Myers Bigel Sibley & Sajovec, P.A.

(57) ABSTRACT

Dry powder inhalers are described with an inhaler body defining an enclosed cavity space and at least one of (a) an endless strip having opposing primary surfaces, the strip comprising a plurality of spaced apart blisters or dose containers holding dry powder medicament. The inhaler also has an inhalation exit flow path in the inhaler body in communication with at least one blister or at least one dose container held by the strip in a dispensing position and a piercer configured to release dry powder medicament from the blister or dose container in the dispensing position.

20 Claims, 21 Drawing Sheets

(56) References Cited

U.S. PATENT DOCUMENTS

Figure 1:
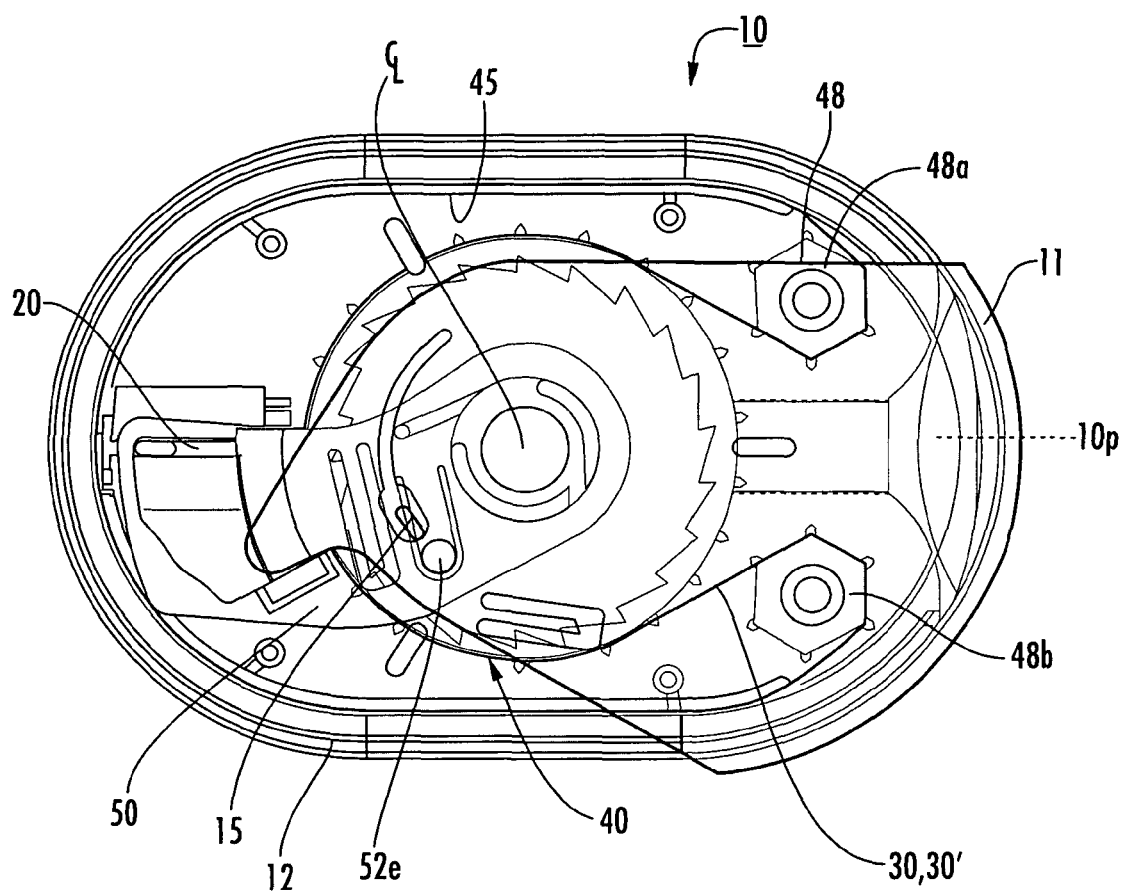

| | | |
|---|---|---|
| 6,536,427 B2 | 3/2003 | Davies et al. |
| 6,971,383 B2 | 12/2005 | Hickey et al. |
| 7,025,056 B2 | 4/2006 | Eason et al. |
| 8,443,798 B2 * | 5/2013 | Eason et al. ............. 128/203.12 |
| 8,511,304 B2 * | 8/2013 | Anderson et al. ........ 128/203.25 |
| 2001/0007853 A1 | 7/2001 | Dimarchi et al. |
| 2001/0053761 A1 | 12/2001 | Dimarchi et al. |
| 2007/0131225 A1 * | 6/2007 | Rand ........................ 128/200.23 |
| 2007/0137645 A1 | 6/2007 | Eason et al. |
| 2008/0099016 A1 | 5/2008 | Pocock et al. |
| 2009/0013994 A1 | 1/2009 | Jones et al. |
| 2009/0194105 A1 | 8/2009 | Besseler et al. |
| 2010/0197565 A1 | 8/2010 | Smutney et al. |
| 2011/0094507 A1 * | 4/2011 | Wachtel et al. .......... 128/200.21 |
| 2013/0032144 A1 * | 2/2013 | Miller et al. ............. 128/203.12 |

\* cited by examiner

DRY POWDER INHALERS WITH ENDLESS STRIPS AND COOPERATING PIERCERS AND RELATED METHODS

RELATED APPLICATIONS

This application is a 35 USC 371 national phase application of PCT/US2009/005335, filed Sep. 25, 2009, which claims the benefit of and priority to U.S. Provisional Patent Application No. 61/101,175, filed Sep. 30, 2008, the disclosures of which are incorporated herein by reference as if set forth in their entirety.

FIELD OF THE INVENTION

The present invention relates to inhalers, and may be particularly suitable for dry powder inhalers.

BACKGROUND

Dry powder inhalers (DPIs) are an alternative to pMDI (pressurized metered dose inhaler) devices for delivering drug aerosols without using propellants. Typically, DPIs are configured to deliver a powdered drug or drug mixture that includes an excipient and/or other ingredients. Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose.

In operation, DPI devices strive to administer a uniform aerosol dispersion amount in a desired physical form of the dry powder (such as a particulate size) into a patient's airway and direct it to a desired deposit site(s).

A number of obstacles can undesirably impact the performance of the DPI. For example, the small size of the inhalable particles in the dry powder drug mixture can subject them to forces of agglomeration and/or cohesion (certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Examples of known prior art inhalers include U.S. Pat. No. 6,536,427 to Davies et al. which proposes inhalers with blister strips that are peeled apart to expose the dry powder and U.S. Patent Application Publication No. 2007/0137645 which proposes an inhaler with a strip of blisters, each having a lid that is puncturable. U.S. Pat. No. 7,025,056 to Eason et al. proposes an inhaler for producing an inhalable aerosol of a powdered medicament that includes an aerosolizing device in the form of a vortex chamber.

Notwithstanding the above, there remains a need for alternative inhalers and/or airways for dry powders.

SUMMARY

Embodiments of the invention are directed to inhalers with continuous (e.g., endless) strips or loops of dry powder medicament in spaced apart blisters or other dose containers.

Some embodiments are directed to dry powder inhalers with an inhaler body defining an enclosed cavity space and at least one of (a) an endless blister strip having opposing primary surfaces, the blister strip including a plurality of spaced apart blisters holding dry powder medicament. The inhaler also has an inhalation exit flow path in the inhaler body in communication with at least one blister or at least one dose container held by the strip, respectively, in a dispensing position and a piercer configured to release dry powder medicament from the blister or dose container in the dispensing position.

Some embodiments are directed to dry powder inhalers that include: (a) an inhaler body defining an inner cavity; (b) an endless strip having opposing primary surfaces held in the inhaler body cavity, the strip comprising a plurality of spaced apart blisters and/or dose containers holding dry powder medicament; (c) an inhalation exit flow path in the inhaler body in communication with at least one blister or at least one dose container, respectively, in a dispensing position; (d) a piercer in the inhaler body, the piercer configured to open the blister or dose container in the dispensing position; and (e) at least three guide members spaced apart about a perimeter of the inhaler cavity body that cooperably engage the strip and hold the strip in a shape that has a semi-circular inner portion that merges into a curvilinear outer portion while allowing the strip to rotate in the inner cavity to position blisters and/or dose containers to the dispensing position.

Yet other embodiments are directed to dry powder inhalers that include: (a) an inhaler body defining an enclosed cavity; (b) an endless strip of blisters held in the cavity of the inhaler body, the strip having opposing primary surfaces, the dose containers or the blisters comprising dry powder medicament, wherein the strip is held in the cavity space of the inhaler body with the primary surfaces thereof oriented in a fixed substantially vertical orientation; (c) an inhalation exit flow path in the inhaler body in communication with a dose container or blister in a dispensing position; (d) a piercer configured to radially reciprocate in a direction that is substantially orthogonal to the primary surfaces of the strip in the dispensing position to release the dry powder medicament of a respective dose container or blister in the dispensing position; (e) an inner guidewall residing in the inhaler body cavity space having at least one open space aligned with the piercer; (f) a rotating member residing above or under the inner guidewall that engages the strip and rotates respective dose containers into position so that a respective dose container or blister in the dispensing position resides between the open space of the inner guidewall and the piercer; (g) an outer guidewall residing in the inhaler body cavity spaced apart from the inner guidewall proximate an outer wall of the inhaler body; and (h) a pair of spaced apart rotatable posts in the inhaler body cavity, one on each side of the exit flow path. The inner guidewall, the outer guidewall and the posts cooperate to hold the strip in a curvilinear shape and allow the r strip to rotate to place respective dose containers or blisters in the dispensing position.

In some particular embodiments, the delivery flow path can include a delivery tube with an inner wall/surface having a polygonal configuration defined by a plurality of elongated planar surfaces oriented substantially parallel with a longitudinal axis of the delivery tube. Angles between adjacent elongated planar surfaces can be, for example, greater than or equal to about one-hundred five degrees (105°), greater than or equal to about one-hundred twenty degrees (120°), greater than or equal to about one-hundred thirty-five degrees (135°), etc. For example, the tube wall inner surface can have a hexagonal configuration with six (6) planar surfaces and wherein the angle between adjacent planar surfaces is one-hundred twenty degrees (120°). In some embodiments, substantially the entire tube wall inner surface can have a polygonal configuration.

The polygonal configuration of the tube wall inner surface can cause a cyclonic air stream to bounce off the planar surfaces multiple times as the air stream flows through the delivery tube. The multiple impacts combined with the shear forces imparted by the cyclonic air stream may facilitate deagglomeration of dry powder medicament entrained within the air stream. As such, the delivery tube serves as an effective deagglomeration chamber for deagglomerating dry powder medicament being inhaled therethrough by a user.

Other embodiments are directed to methods of operating an inhaler. The methods include: (a) translating an endless strip of blisters or dose containers having a fixed perimeter shape with an obround outer portion that merges to an inner circular portion to both serially position respective dose containers or blisters in a defined dispensing position in the inhaler and move empty dose containers or blisters away from the dispensing position; (b) rotating at least one member having outwardly extending tabs that engage the strip to carry out the translating step; (c) translating a piercer toward a dose container or blister in the dispensing position to open and release dry powder medicament therefrom; and (d) capturing the released medicament in an exit flow path.

The translating step can optionally be carried out by radially translating the piercer between three positions during a piercing step, a home retracted first position, a radially translated first forwardmost position, and a third partially radially retracted position, such that the piercer blocks an opening formed in the blister/dose container or a port associated with an exit airflow path when the piercer is in the third position.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly including the right to be able to amend any originally filed claim to depend from and/or incorporate any feature of any other claim although not originally claimed in that manner. These and other objects and/or aspects of the present invention are explained in detail in the description set forth below.

BRIEF DESCRIPTION OF THE DRAWINGS

FIG. 1 is a top view of an inhaler with a cover according to some embodiments of the present invention.

FIG. 2 is top view of the inhaler shown in FIG. 1 with the cover in an exemplary open position according to some embodiments of the present invention.

FIG. 3 is an exploded top perspective view of the inhaler shown in FIG. 1 according to embodiments of the present invention.

FIG. 4 is an exploded side perspective view of the inhaler shown in FIG. 1 according to embodiments of the present invention.

FIG. 5 is an exploded side perspective view of the inhaler shown in FIG. 1 (with two blister strips) according to embodiments of the present invention.

FIG. 6 is a top perspective view of a portion of the inhaler shown in FIG. 1 according to embodiments of the present invention.

FIG. 7A is a portion of the inhaler shown in FIG. 6, but without the inner and outer guidewalls according to embodiments of the present invention.

FIG. 7B is a schematic front view illustration of a portion of a blister strip according to some embodiments of the present invention.

FIG. 7C is a top (end) view of the blister strip shown in FIG. 7B.

FIG. 7D is a schematic front view illustration of a portion of a dose container strip according to some embodiments of the present invention.

FIG. 7E is a top (end) view of the blister strip shown in FIG. 7D.

FIG. 8 is a side perspective top view of an exemplary lower portion of an inhaler body according to embodiments of the present invention.

FIG. 9A is a top perspective view of the inhaler shown in FIG. 1 with the upper inhaler housing omitted for ease of discussion.

FIG. 9B is a top perspective view of the inhaler shown in FIG. 1 illustrated with partially transparent components for ease of discussion.

FIGS. 10A and 10B are sequential top views of the inhaler shown in FIG. 1. FIG. 10A illustrates an exemplary pierce configuration and FIG. 10B illustrates an exemplary delivery (post-pierce) configuration according to embodiments of the present invention.

FIG. 10C illustrates the inhaler shown in FIG. 10B after delivery of the medicament in a return and piercer release configuration according to embodiments of the present invention.

FIG. 11A is a top perspective view of the inhaler shown in FIGS. 1, 2 and 10A-10C (without the cover) according to embodiments of the present invention.

FIG. 11B is a bottom side perspective view of a cover for the inhaler shown in FIG. 11A according to embodiments of the present invention.

FIG. 11C is a top perspective view of the inhaler shown in FIG. 11A without the cover and top of the inhaler housing according to embodiments of the present invention.

FIG. 11D is a greatly enlarged view of the tongue shown in FIG. 11C.

FIG. 12 is a side perspective view of an exemplary delivery flow tube according to embodiments of the present invention.

FIG. 13 is a sectional view of the tube wall taken along lines 13-13 in FIG. 12 according to some embodiments of the present invention.

FIG. 14 is side section view of the delivery tube of FIG. 12 illustrating an exemplary polygonal inner surface thereof.

FIG. 15 is an enlarged partial section view of the inlet end of the elongated delivery tube of FIG. 12.

FIG. 16 is a flow chart of exemplary operations for a dry powder inhaler according to some embodiments of the present invention.

FIG. 17 is an exploded view of an inhaler with the piercer configured to translate outwardly and the dispensing position being in an outer row of the strip path according to embodiments of the present invention.

DETAILED DESCRIPTION

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various components, regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise. For example, the terms are used to describe and/or claim the relative orientations of features as shown in the drawings (and are typically associated with a normal "use" position/orientation).

In the description of the present invention that follows, certain terms are employed to refer to the positional relationship of certain structures relative to other structures. As used herein, the term "front" or "forward" and derivatives thereof refer to the general or primary direction that dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "radial" with respect to movement of the piercer means to move toward and/or away from a center or medial point of the inhaler body. The term "rotate" with respect to the movement of the strip in the inhaler refers to the fixed order of succession in which the strip moves in the inhaler to carry out a complete cycle of motion.

The term "deagglomeration" and its derivatives refer to processing dry powder in the inhaler airflow path to inhibit the dry powder from remaining or becoming agglomerated or cohesive during inspiration.

The term "dead zone" refers to a localized area of low flow and/or pressure within a dry powder delivery tube/conduit of an inhaler.

The term "obround" shape refers to an elongate shape having semicircular ends spaced apart by respective parallel (substantially straight) lines.

The term "endless" with respect to the blister strip means the strip end portions are attached (directly or indirectly) together to form a continuous strip and/or loop. Similarly, the term "loop" can be used interchangeably with the phrase "endless strip" and means that the carrier is joined (directly or indirectly) at the end portions (e.g., having a closed shape) with no particular limitation as to the shape thereof. Thus, an endless strip can have a constant perimeter shape and can be configured to use the same space twice, once for "full" blisters/dose containers and one for used or empty dose containers/blisters.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers.

The terms "sealant", "sealant layer" and/or "sealant material" includes configurations that have at least one layer of at least one material; thus, such a phrase also includes multilayer or multi-material sealant configurations. Thus, term "sealant layer" includes single and multiple layer materials, typically comprising a foil layer. The sealant layer can be a thin multi-layer laminated sealant material with elastomeric and foil materials. The sealant layer can be selected to provide drug stability as they may contact the dry powder in the respective dose containers.

The sealed dose containers and/or blisters can be configured to inhibit oxygen and moisture penetration to provide a sufficient shelf life.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 g/cm3 or less. In particular embodiments, the low-density powder may have a density of about 0.5 g/cm3 or less. The dry powder may be a dry powder with cohesive or agglomeration tendencies.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligonucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed. See e.g., Wolff et al., Generation of Aerosolized Drugs, J. Aerosol. Med. pp. 89-106 (1994). See also U.S. Patent Application Publication No. 20010053761, entitled Method for Administering ASPB28-Human Insulin, and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, 8-agonists (including long-acting 8-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

The inhalers can be configured to provide any suitable number of doses, typically between 30-120 doses, and more typically between about 30-60 doses. The inhalers can deliver one or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

Turning now to the figures, FIG. 1 illustrates an example of a multi-dose inhaler 10 with a cover 11, housing 12, and inhalation port 10p. This inhaler configuration is shown merely for completeness and embodiments of the invention are not limited to this inhaler configuration as other form factors, covers and inhalation port configurations may be used. The inhaler 10 includes a plurality of spaced apart strip guide members that help hold the strip 30, 30' in a desired orientation, such as with a semi-inner circular inner portion held inwardly of a curvilinear outer portion. The strip can be flexible and take on a configuration so that it occupies two or more rows in the inhaler cavity (e.g., it can loop or double back on itself). The guide members can include rotating and stationary members that guide the blisters/dose containers 30b, 30d to the dispensing position.

Figure 2:
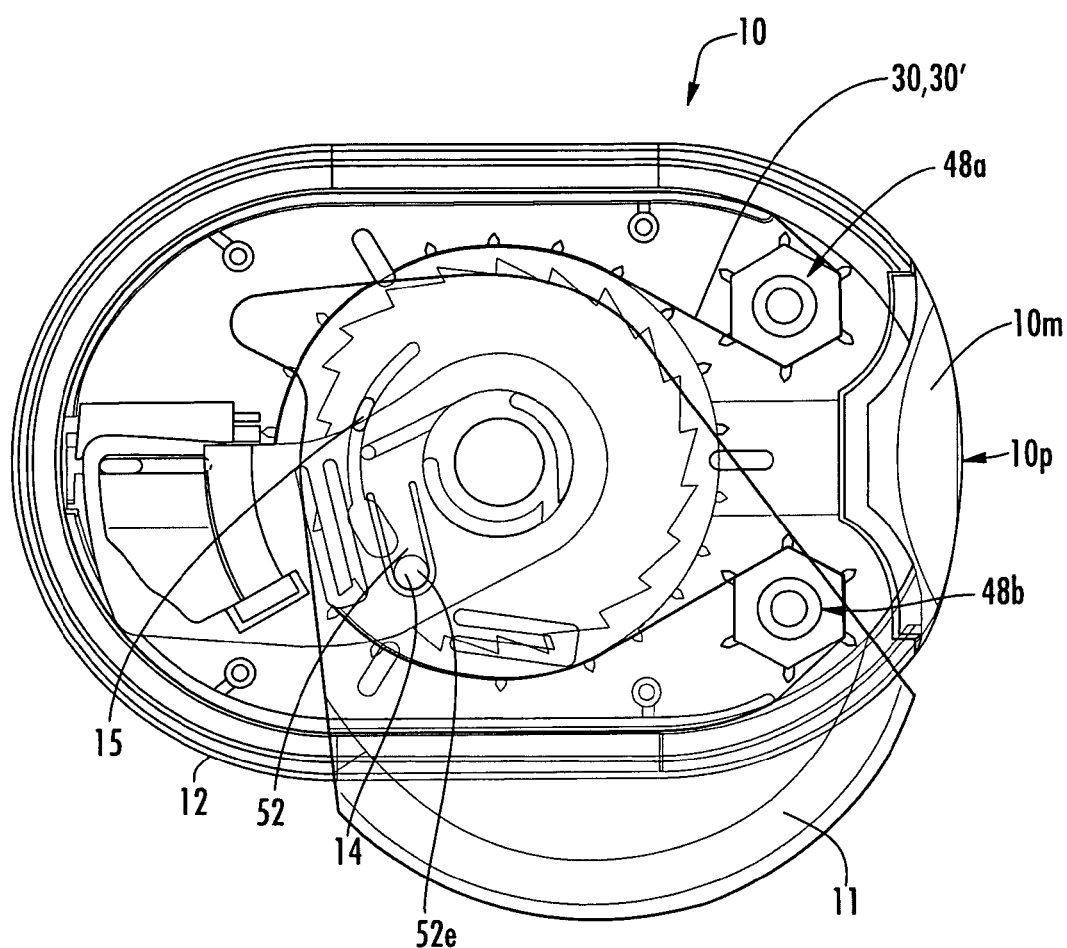

FIG. 1 shows the inhaler with the cover 11 in a "closed" or non-use configuration with the cover 11 residing over the mouthpiece associated with the inhalation port 10p. FIG. 2 shows the cover 11 rotated to the side of the inhaler housing or body 12 revealing the inhalation port 10p and mouthpiece 10m.

Figure 3:
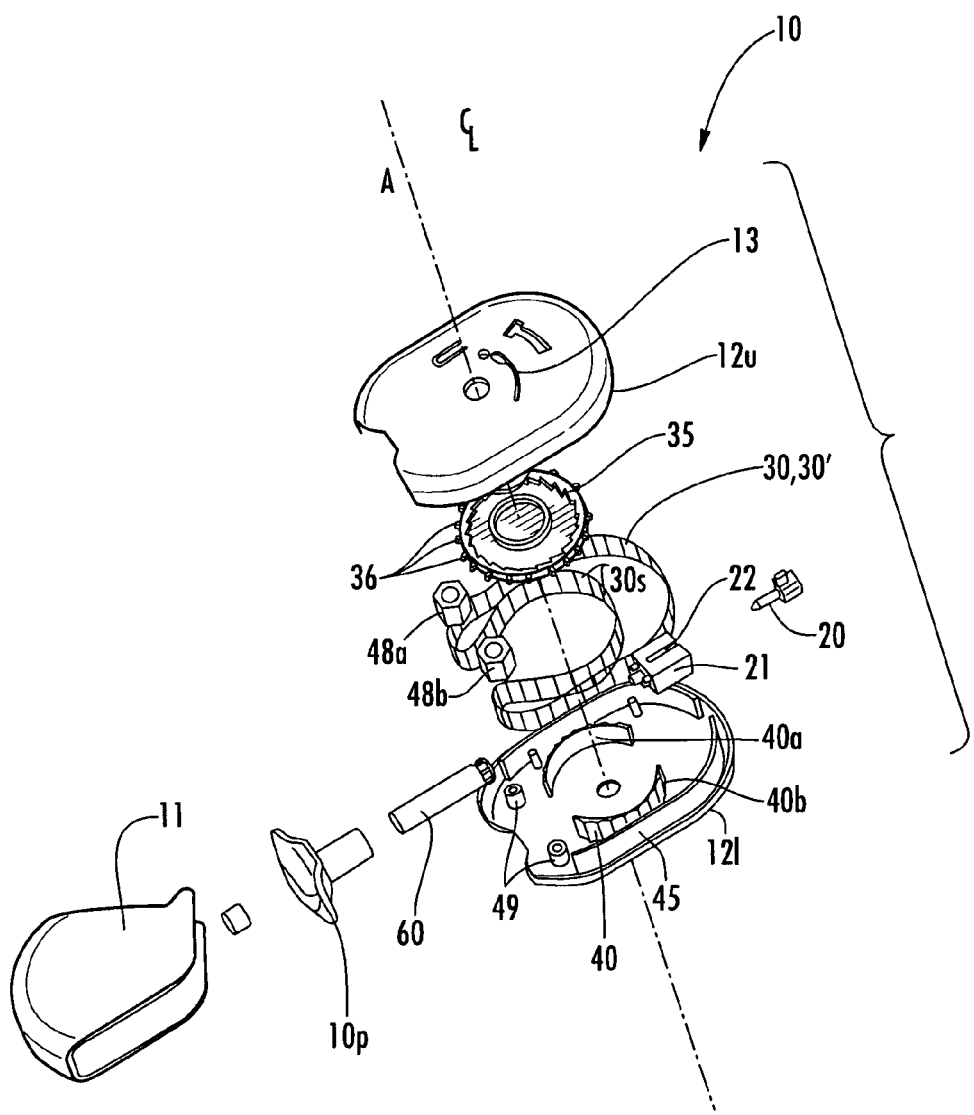
Figure 6:
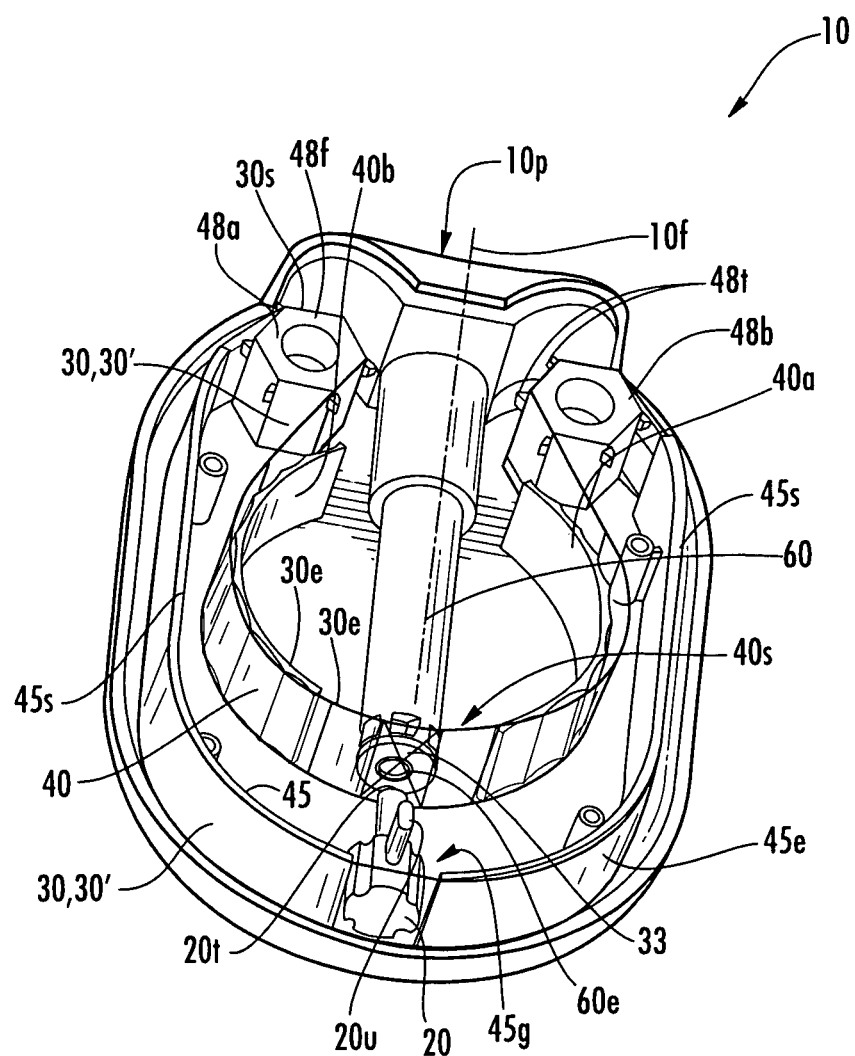

FIGS. 1 and 2 are shown with the top of the housing 12 transparent so that components therein can be more easily described. FIG. 3 is an exploded view of the components. Referencing FIG. 3, the inhaler 10 can include an endless curvilinear blister strip 30 of blisters 30b or endless strip 30' of dose containers 30d. That is, although described or shown primarily herein with respect to the strip 30 being a blister strip of spaced apart blisters 30b (FIGS. 7B, 7C), the strip may also or alternatively include spaced apart dose containers 30d (FIGS. 7D, 7E). The dose containers 30d can include a sealant or other material that holds the dry powder medicament therein and is configured to allow a piercer to open the respective dose container 30d in a target dispensing position 33 marked with an "X" as shown in FIG. 6. The dose container 30d (FIGS. 7D, 7E) can have any appropriate configuration and may include upper and lower sealants attached to a frame with increased rigidity (typically at least about 5×-10× or of the rigidity) relative to the sealants that hold the dry powder therein.

As shown in FIGS. 1-4, the inhaler 10 can also include a piercer 20, a rotatable (center) member 35, an inner guidewall 40 and an outer guidewall 45, and a plurality of posts 48a, 48b (shown as two posts). The inner and outer guidewalls 40, 45 may be configured as posts, tabs, slots in channels, or other structural support members that engage and/or hold the strip 30, 30' in the desired configuration.

The inner guidewall 40 can optionally be configured as a pair of spaced apart semi-circular upwardly extending walls 40a, 40b with ends thereof residing spaced apart from each other. Other configurations of the inner guidewall 40 are possible. Where the piercer is translated inwardly to pierce, the inner member(s) can be configured to allow the piercer 20 to extend through a dose container 30d or blister 30b in the dispensing position which is adjacent the piercer 20 (e.g., have a gap, channel, aperture or the like). In operation, the piercer 20 can radially translate toward the dispensing position to pierce/puncture or otherwise open a blister 30b and/or dose container 30d to release the medicament into a delivery flow path 10f (FIG. 6). The piercer 20 can be spring loaded so that upon release of a force holding or pushing it toward the endless strip 30, 30', it automatically retracts.

The strip 30, 30' can have a constant perimeter shape with primary surfaces thereof being substantially vertical as the strip moves through the inhaler to release medicament from different blisters or dose containers. The strip 30, 30' can optionally be held in tension, but is typically held substantially snugly against the outer guidewall, the inner guidewall and the posts 48a, 48b. The strip 30, 30' rotates through the inhaler cavity about these members to (serially) position blisters 30b or dose containers 30d in the dispensing position 33 (FIG. 6). During use (over time), the strip 30, 30' will have a mixture of "full" and "empty" blister or dose container segments until the strip 30, 30' is depleted of medicament at which time the strip or loop 30, 30' will have all empty segments. However, the strip 30, 30' will typically have substantially the same endless perimeter shape in the inhaler 10 irrespective of whether it is full, partially full or empty.

The rotating (center) member 35 may reside on the upper portion of the inner guidewall 40. The rotating member 35 can be circular and include a plurality of circumferentially spaced apart tabs 36. The rotating member 35 can have a center of rotation "A" that is coincident with that of the cover 11. The tabs 36 can engage the strip 30, 30' and rotate the strip to position blisters 30*b* or dose containers 30*d* into the dispensing position 33 (shown by the "X" in FIG. 6). The inhaler 10 may also optionally include a pivoting/rotating tongue 50 that rotates about the same axis of rotation as that of the rotating member 35 and cover 11 that moves the radial piercer 20 into position as will be discussed further below.

Figure 4:
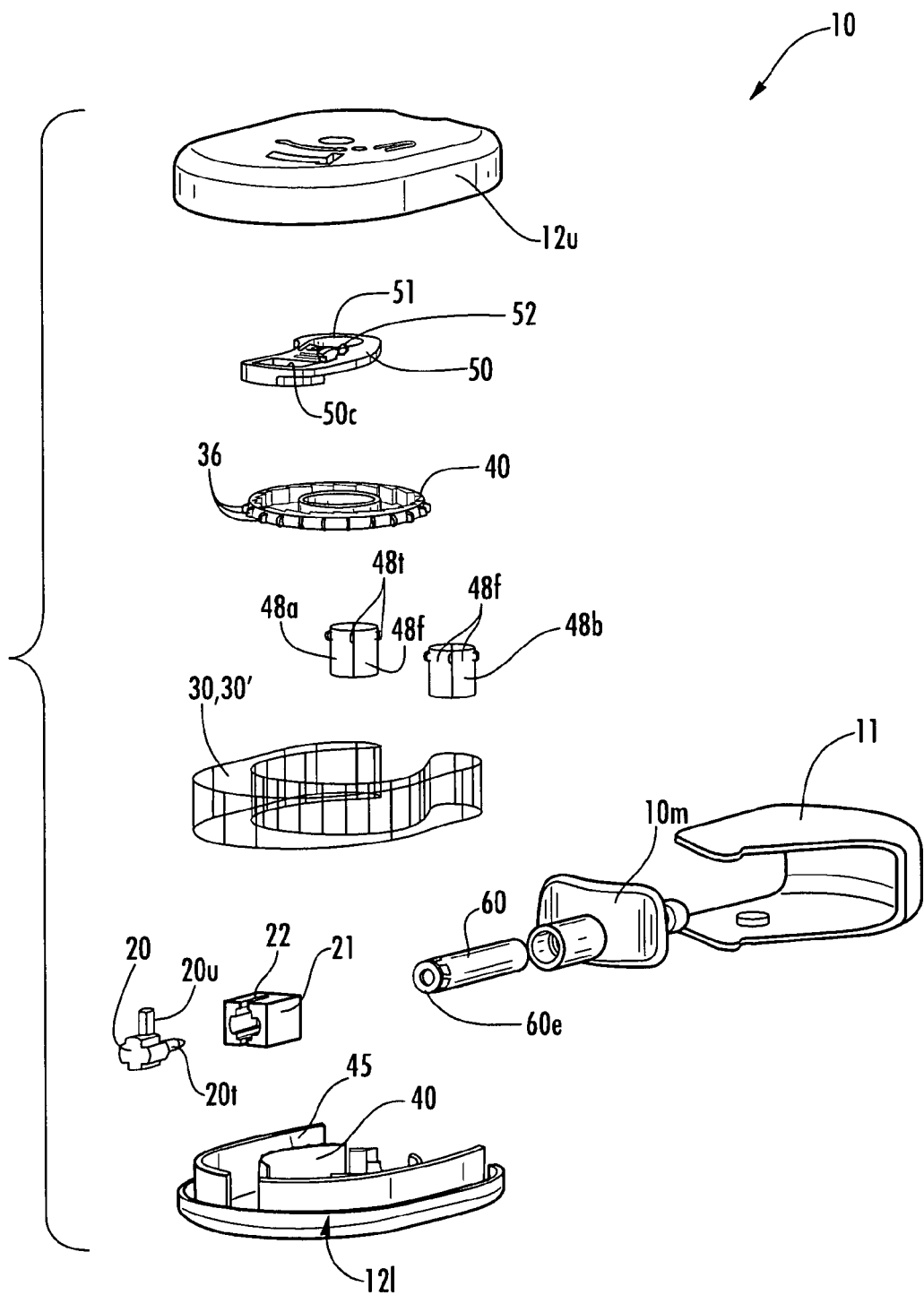

As also shown in FIGS. 3 and 4, the inhaler 10 can include a tubular conduit 60 that defines at least a portion of the delivery flow path. As shown in FIG. 6, the tubular conduit (e.g., delivery tube) 60 can reside between the semi-circular walls 40*a*, 40*b* and be in fluid communication with the inhalation port 10*p*. One end of the tubular conduit 60 can face the piercer 20 and the other can face the inhalation port 10*p*.

Referring to FIGS. 3 and 4, the inhaler housing or body 12 can include matable upper and lower members, 12*u*, 12*l*, respectively. The inner and outer guidewalls 40, 45 can be molded and/or otherwise be formed to be integral to the lower housing 12*l*. The posts 48*a*, 48*b* can be rotatable and can slidably mount over upwardly projecting mount tubes 49 molded or otherwise formed into the lower housing. The guidewalls 40, 45 and/or the mount tubes 49 may alternatively be mounted to the upper housing although not shown.

Figure 5:
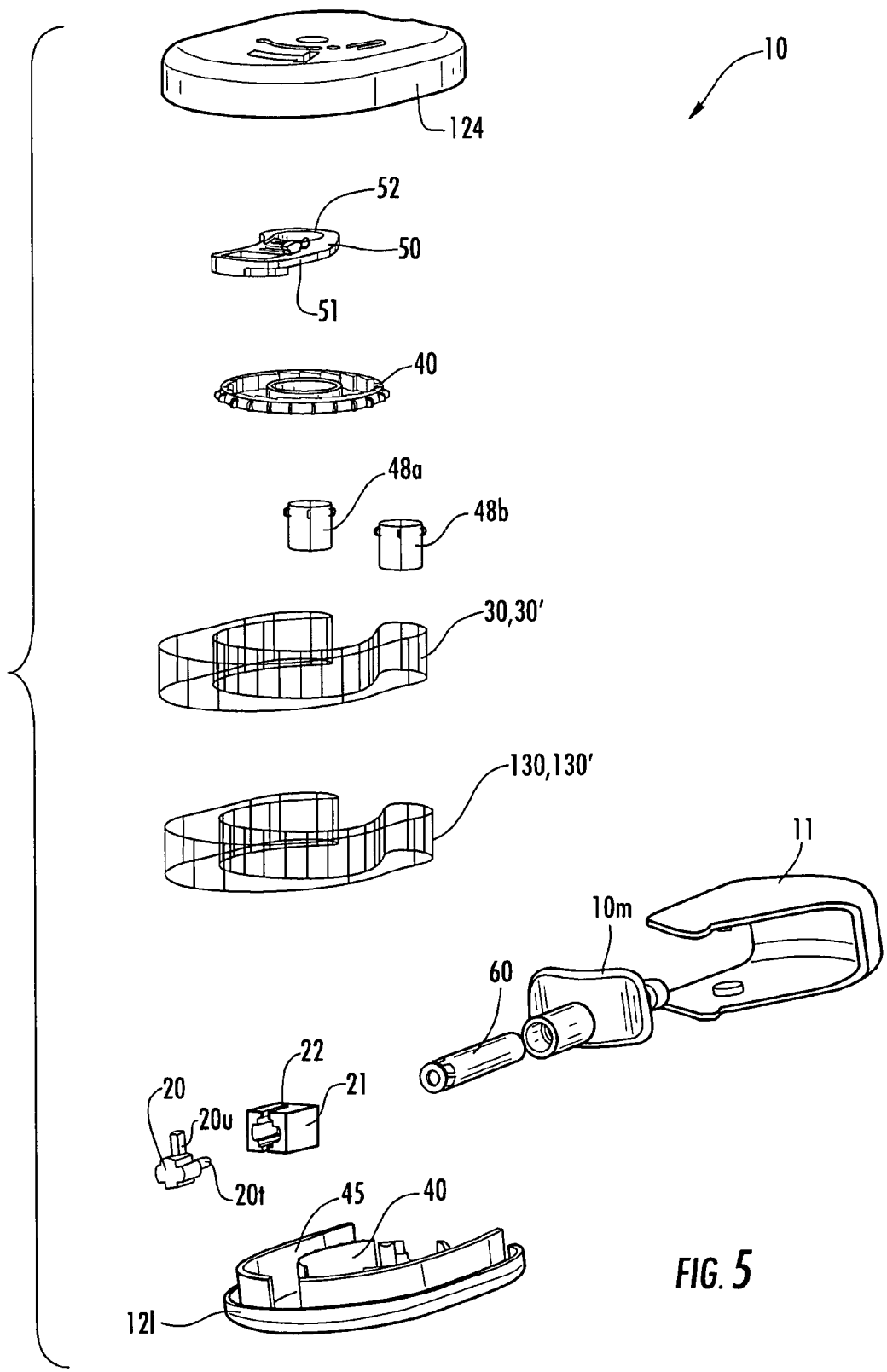

FIG. 5 illustrates that the inhaler 10 can include first and second endless strips 30 (30'), 130 (130') of blisters 30*b* or dose containers 30*d*. Each strip can hold the same or a different medicament. If the latter, the different medicaments can be configured for concurrent delivery of combined medicines. Each strip 30 (30'), 130 (130') can be configured with alternating different medicaments and/or blanks to allow a single medicament delivery or a medicament dual delivery as desired. The strips can advance in concert in the inhaler housing and may be configured to reside side-by-side (nested back to front or front to back or one above the other, in alignment).

It is also contemplated that each strip 30 (30'), 130 (130') can have blisters/dose containers 30*b*, 30*d* of different medicaments and two blisters/dose containers (one from each strip) can be positioned in the dispensing position X and opened substantially concurrently with a dual head piercer or two closely spaced piercers that release the two medicaments into the delivery path for inhalation. Alternately, the strips 30 (30'), 130 (130') can be configured to alternate or one to dispense all first before the other is used to allow for increased numbers of doses).

Referring to FIG. 6, the posts 48*a*, 48*b* can be polygonal with a plurality of flat facets 48*f* and the posts 48 may be hexagonal as shown. The facet 48*f* size can be such that it holds a respective blister/dose container segment 30*s* thereagainst. Each segment 30*s* can be scored, slit at outer edges 30*e* thereof or otherwise configured or formed to preferentially bend to substantially conform to the shape of the facet 48*f* as the strip segments 30*s* move around surfaces of the posts 48*a*, 48*b* as shown, for example, in FIGS. 2, 6 and 7A. As shown, in operation, the strip 30, 30' conforms to about three facets 48*f* at any one time, trails into or away from another facet 48*f* and does not contact one or more other facets 48*f*.

Still referring to FIG. 6, the piercer 20 can have a piercing tip 20*t* and an upwardly extending portion 20*u*. The tip 20*t* faces one open end 60*e* of the tubular member 60, which resides between an open space 40*s* left by the guidewall 40, with the blister/dose container in the dispensing position therebetween. In operation, the piercer 20 radially reciprocally translates to open the blister/dose container 30*b*, 30*d*, then retracts, typically partially retracts to block/occlude a rearward portion of the blister or dose container such as an opened sealant facing away from the open end of the member 60 (and, in the partially retracted position, where used, may reside proximate a trajectory line drawn connecting the ends of the walls of the center member 40). The two-position retract configuration can be carried out so that upon partial retraction of the piercer 20, the piercer can inhibit/block dry powder from exiting one side of the opened blister/dose container, then fully retract to the home position (shown in FIG. 6). The piercer tip 20*t* is shown as being tapered and solid. However, other piercer configurations may be used including hollow, cork screw shapes, fluted shapes and the like.

It is also contemplated that other airway channels and paths in addition or alternatively to the tubular member 60 can be used as well as other dose container configurations. For example, a side airway channel/path in communication with opened dose containers. In such embodiments, the piercer 20 may also optionally be used to occlude or help direct the medicament out of the inhaler in the side airflow exit path.

Figure 17:
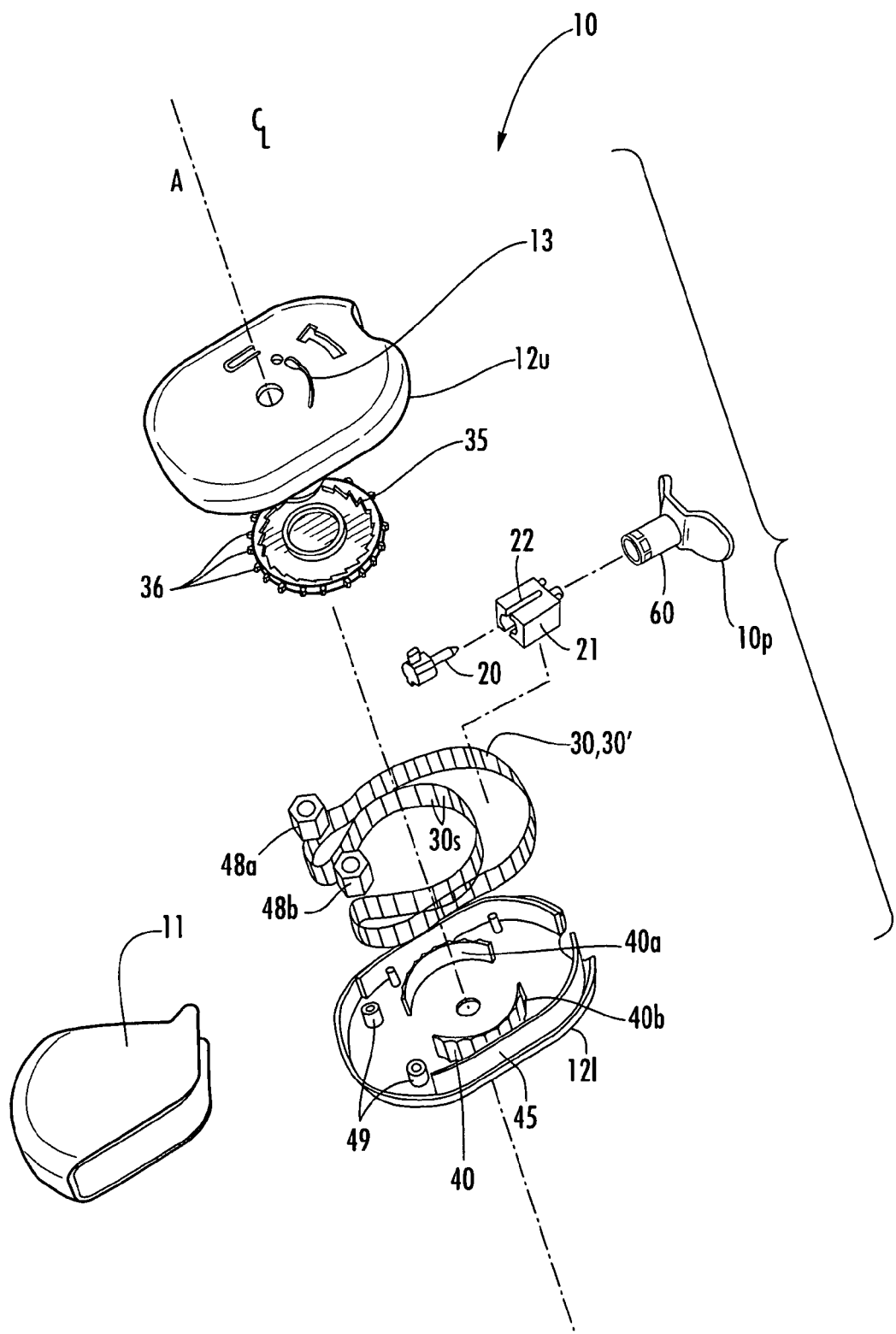

FIG. 17 illustrates that the piercer 20 can be configured to translate radially outward (instead of inward) to pierce blisters/dose containers on the outer row/perimeter. The outer guide structure or member(s) (shown as a wall 45) can have a gap or aperture to allow the piercer to pierce the blister/dose container in the direction of the mouthpiece. The mouthpiece 10*m* can reside on the other side of the piercer 20 and the tubular member 60 can be shorter than that shown in FIG. 3, for example. FIG. 17 also shows that the dispensing position being in an outer row of the strip path according to embodiments of the present invention.

FIG. 6 shows the strip 30, 30' can be obround. Stated differently, the strip 30, 30' can have a semi-circular outer portion and two substantially parallel legs that merge into an inner portion that is circular. Similarly, the outer guidewall 45 can have a semi-circular end portion 45*e* that merges into two elongate substantially parallel straight legs 45*s*, one on each side of the inhaler body 12 that terminate proximate the posts 48*a*, 48*b*. The semi-circular portion 45*e* may have a gap or space 45*g* in a medial portion thereof to accommodate a holder 21 that mounts the piercer 20.

FIG. 6 also shows that the strip 30, 30' can follow a defined continuous path. The strip 30, 30' can reside in the inhaler so that one primary surface contacts a first leg 45*s* of the outer wall of the outer guidewall 45, then goes around the post 48*a*, extends around the outerwall of the inner guidewall 40, the around the other post 48*b*, before extending on the outside of the second leg 45*s* of the outer guidewall, then around the semi-circular portion 45*e* of the outer guidewall 45.

Figure 7A:
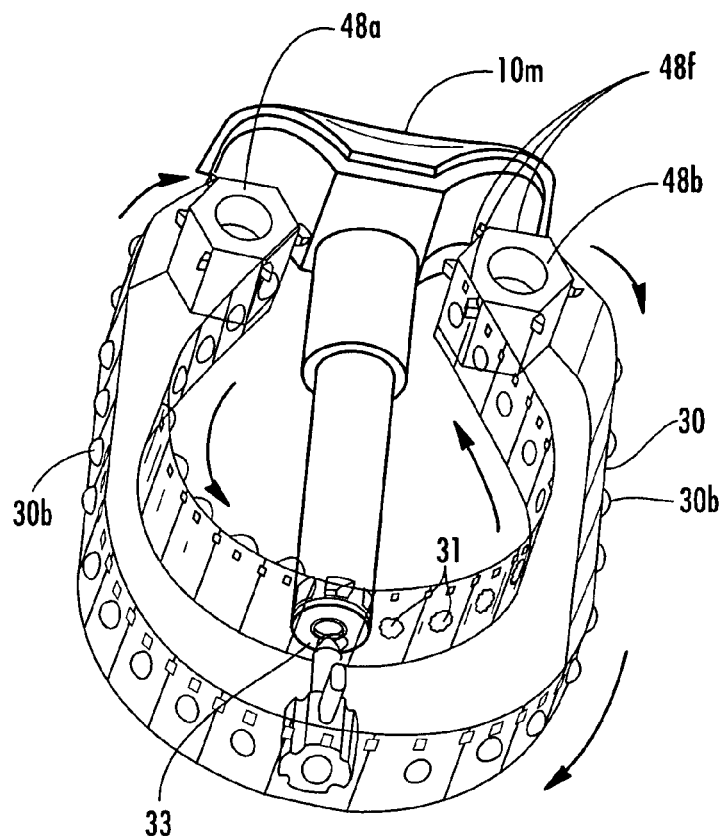
Figure 7B:
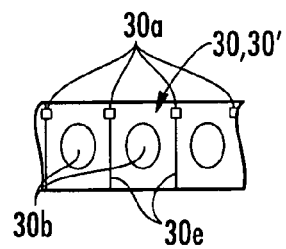
Figure 7C:
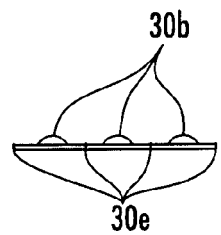
Figure 7E:
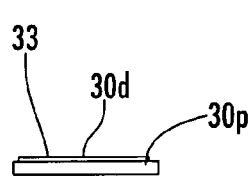
Figure 7D:
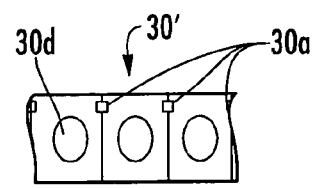
Figure 8:
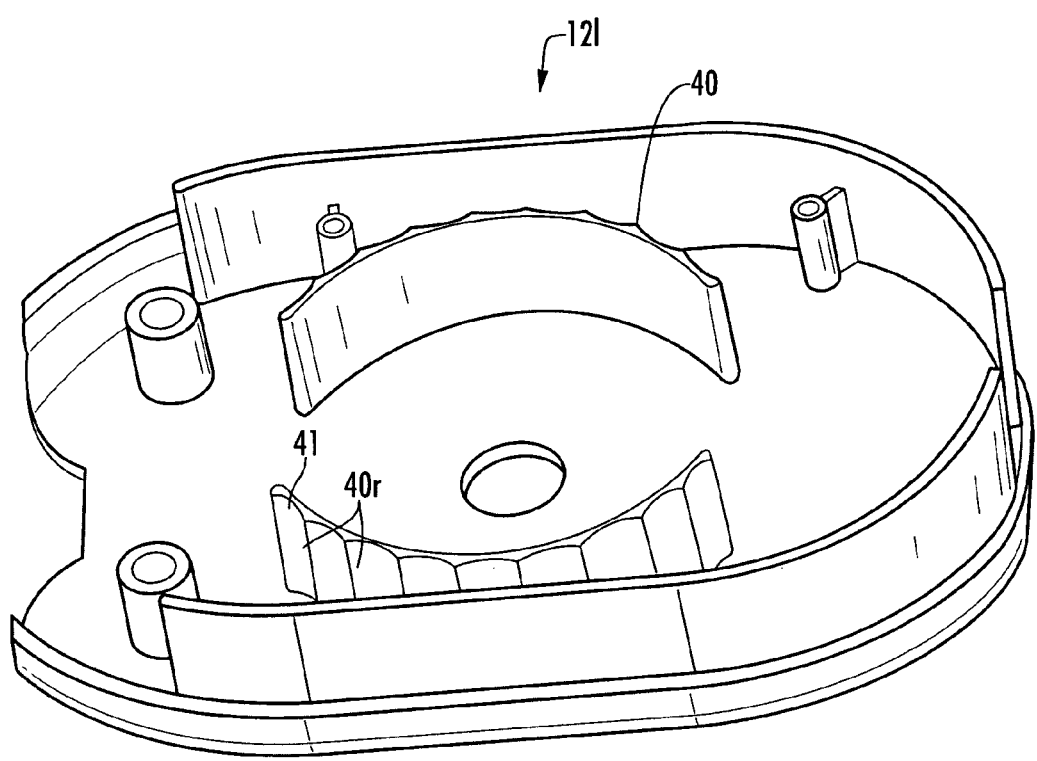

Typically, as shown in FIG. 7A, the primary surface of the strip 30 with the blisters 30*b* faces away from the outer guidewall 45 and the facets 48*f* and into the inner guidewall 40. However, the strip 30 can be oriented in the reverse position as well. The strip 30, 30' can rotate either clockwise or counterclockwise to move the blisters/dose containers into the dispensing position 33. The arrows in FIG. 7A represent an example of the rotational movement. FIG. 7A also shows that the blisters 30*b* are intact as they approach the dispensing position 33 and the strip 30 has apertures 31 due to the piercing of opened blisters or dose containers after (downstream of) the dispensing position. FIG. 7C illustrates that the blisters 30*b* can project outward from one of the primary surfaces thereof and typically face into the wall of the inner guidewall 40. FIG. 7B illustrates that each blister can have edges that are scored or preferentially configured to bend to reside against a facet of the post 48a, 48b. The blister 30b can have a width that matches that of a facet. However, other configurations of blisters and posts may also be used. FIG. 8 illustrates that the outer surface of the guidewall 40 can have a series of adjacent recesses 40r that can receive and/or substantially correspond to the shape of the blister 30b. In other embodiments, the inner guidewall 40 can have other shapes and/or not have the recesses 40r.

FIGS. 7B, 7D illustrate that the strip 30, 30' can include apertures 30a that communicate with tabs 48t on the posts 48a, 48b and tabs 36 on the rotating center member 35. The tabs 36, 48t can be configured to cooperate with apertures on the upper portion of the strip 30, 30' as shown, but may also or alternatively reside on a lower portion (not shown).

FIG. 7D illustrates that the strip 30' of spaced apart dose containers 30d can include apertures 30a as discussed above. FIG. 7E illustrates that the dose containers 30d can include a flexible sealant 33 and a frame or platform 30p with increased rigidity to hold the medicament therein. Other dose container configurations may also be used, but typically the strips 30, 30' are flexible (can be rolled or otherwise configured outside the inhaler body) and able to take on the endless strip shape in position in the inhaler.

Figure 9A:
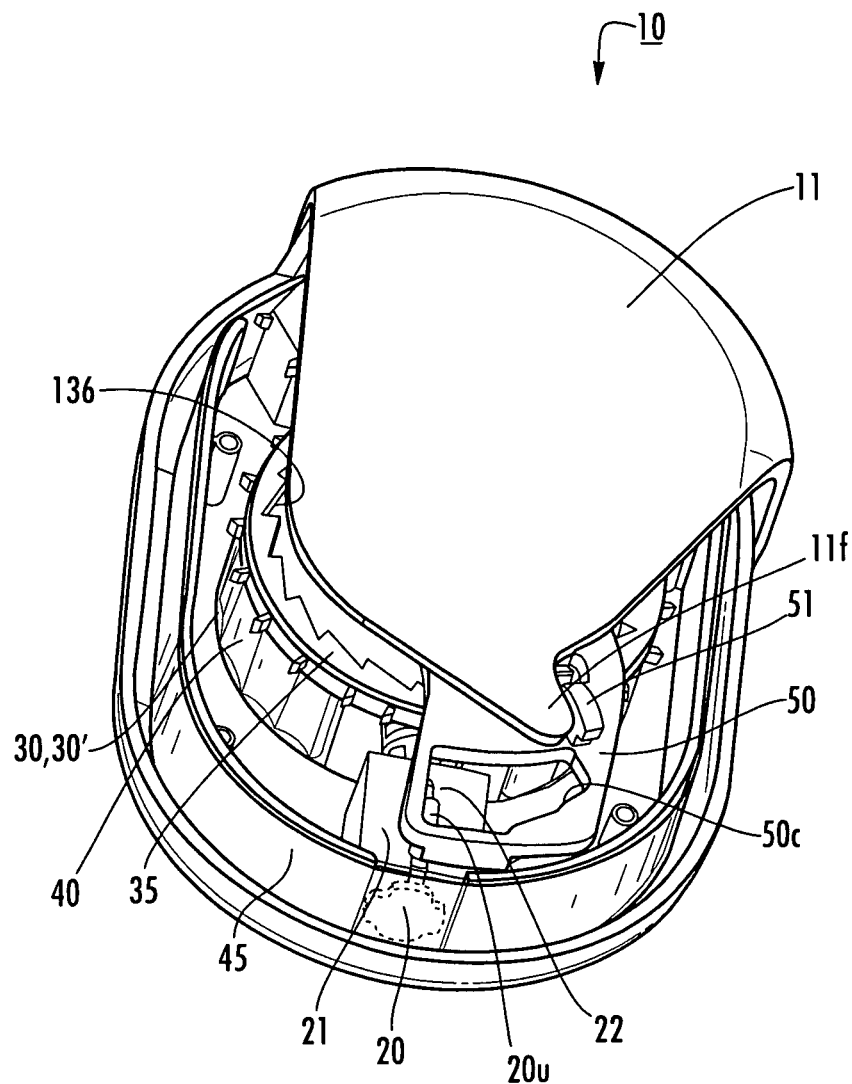

FIG. 9A shows the cover 11 on the inhaler 10 without the upper housing 12u. As shown, the piercer 20 can be held in a block body 21 with a radially extending space or slot 22. The piercer 20 upwardly extending portion 20u (e.g., tab, pin, fin etc. . . . ) resides in the slot 22 and is able to slidably (radially) advance and retract in the slot 22. The block body 21 can be attached to the outer guidewall 45. The upwardly extending member 20u is also in communication with the tongue 50. The tongue 50 can include a cutout space that defines a cam surface 50c. In operation, as the tongue 50 rotates in one direction, the upwardly extending member 20u contacts the varying surface profile of the cam surface 50c and is forced forward in the slot 22, which forces the piercer 20 forward a distance sufficient to pierce/open a dose container or blister 30d, 30b in the dispensing position 33 (FIG. 6). The tongue 50 can be spring loaded using a torsion spring or other resilient member to help drive the desired movement. Other piercer movement devices and/or configurations can be used.

As discussed above, in some embodiments, the piercer 20 is configured to partially retract a defined distance (just after active piercing) and hold during a delivery of the released medicament. This action allows the piercer tip 20t to extend into a first pierced sealant of a dose container or blister (where two sealants are used) so that the piercer tip 20t or upstream portion of the piercer occludes, blocks or inhibits the dry powder from exiting out of this side or end of the blister/dose container. When the tongue 50 rotates in the other direction, the upwardly extending member 20u can return to the "home" position, e.g., at a radially retracted position.

Figure 10A:
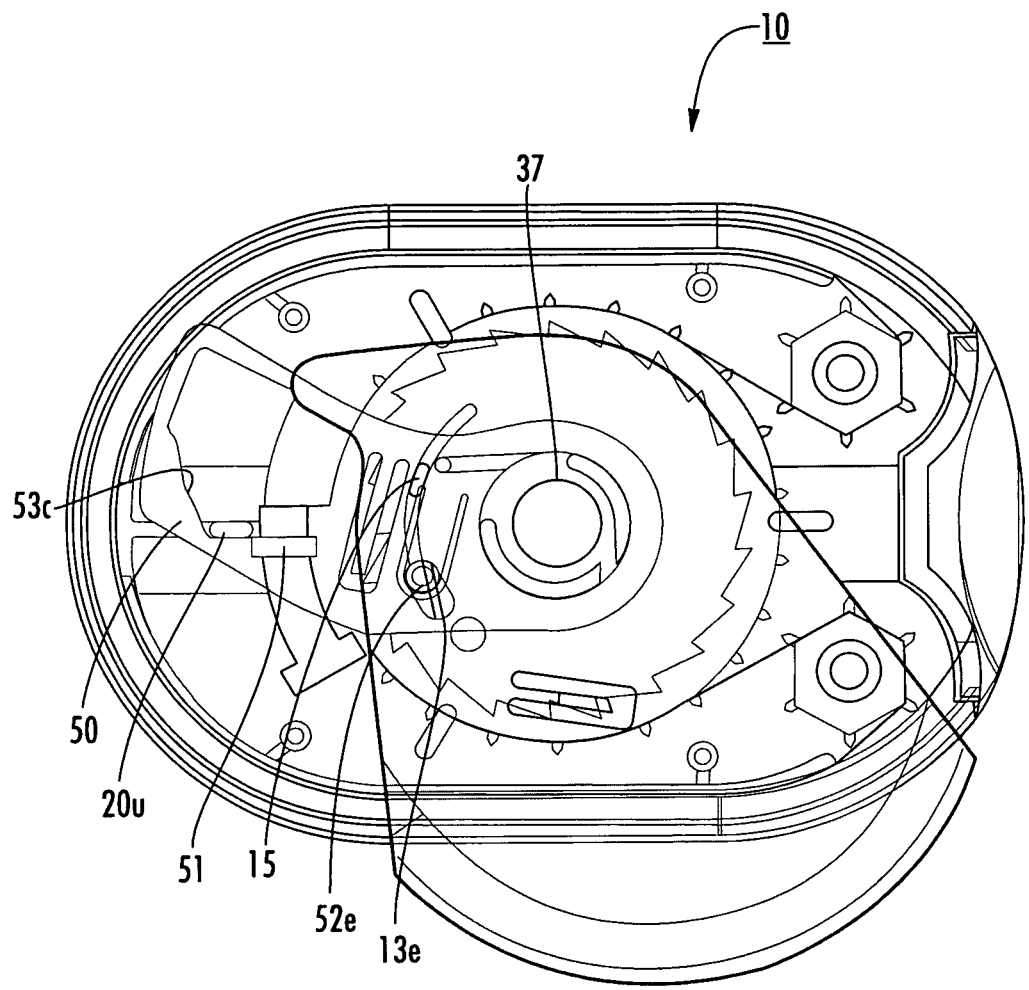
Figure 10B:
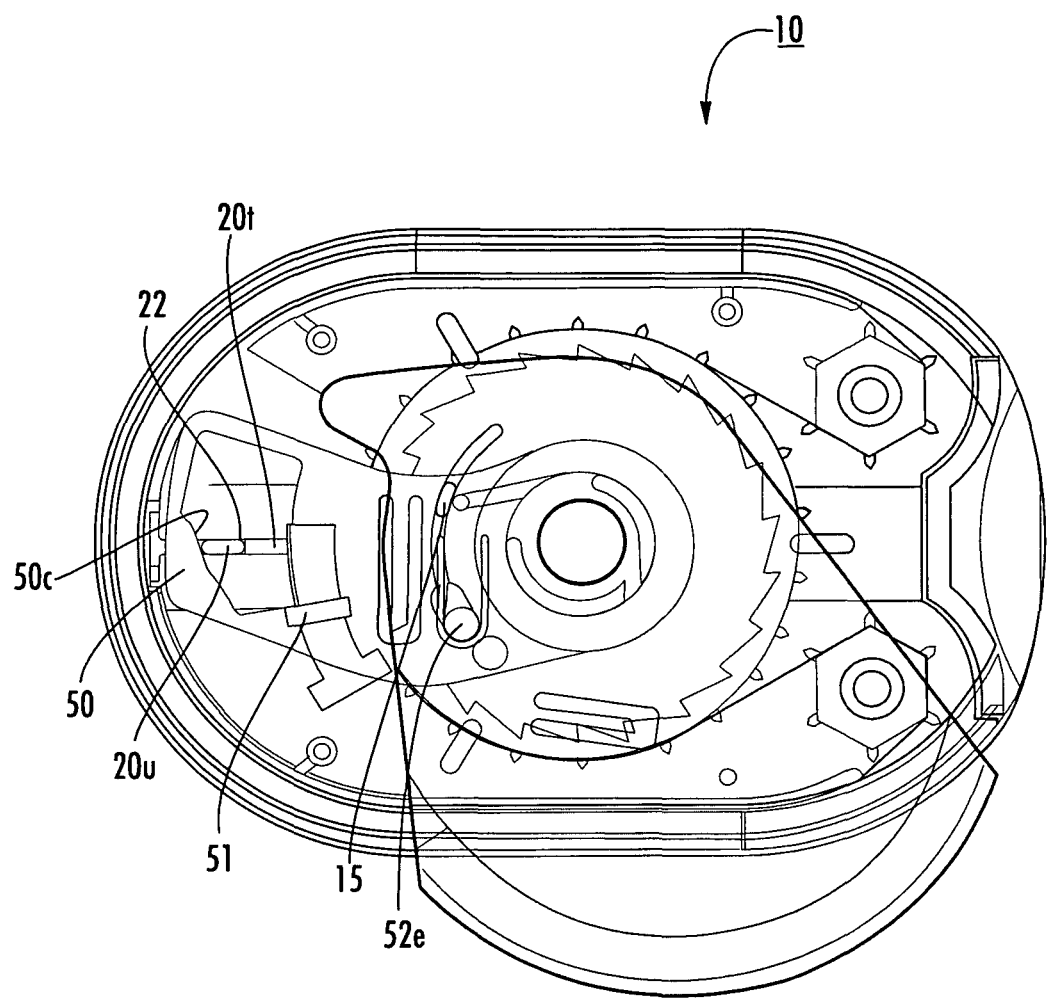
Figure 10C:
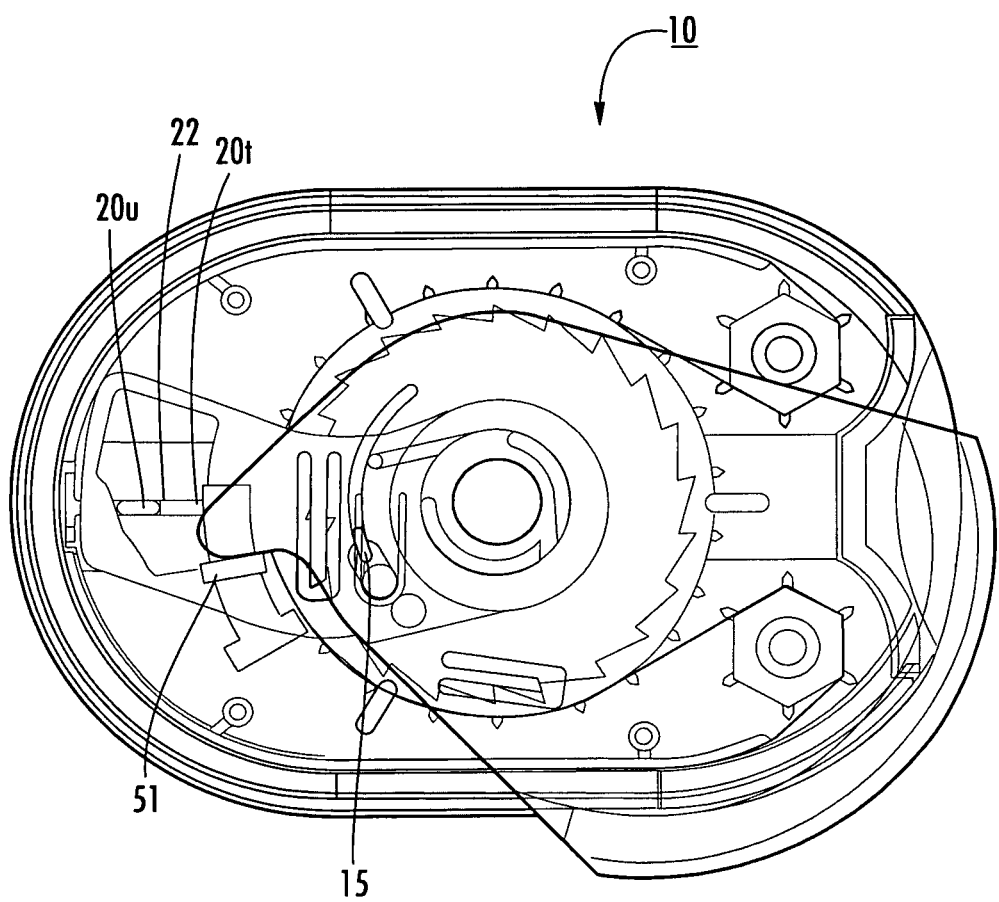

FIG. 10A illustrates an exemplary position of the piercer 20, tongue 50 and cam surface 50c in a "piercing" configuration with the piercer 20 at a forwardmost position in the slot 22. FIG. 10B illustrates an exemplary position of the piercer 20, tongue 50 and cam surface 50c in a "delivery" configuration with the piercer 20 partially radially retracted. FIG. 10C illustrates a "return" release of the piercer 20 so that as the cover 11 is rotated to close (FIG. 1), a cover extension or finger 11f (FIG. 9A) pushes the lever 51 back to a home position which pulls the cutout with it and allows the piercer 20 to radially retract within the more open profile portion of the cam surface 50c. FIGS. 1 and 2 illustrate the piercer in a fully retracted "home" position (FIG. 1 with the cover 11 closed and FIG. 2 with the cover 11 open).

Figure 9B:
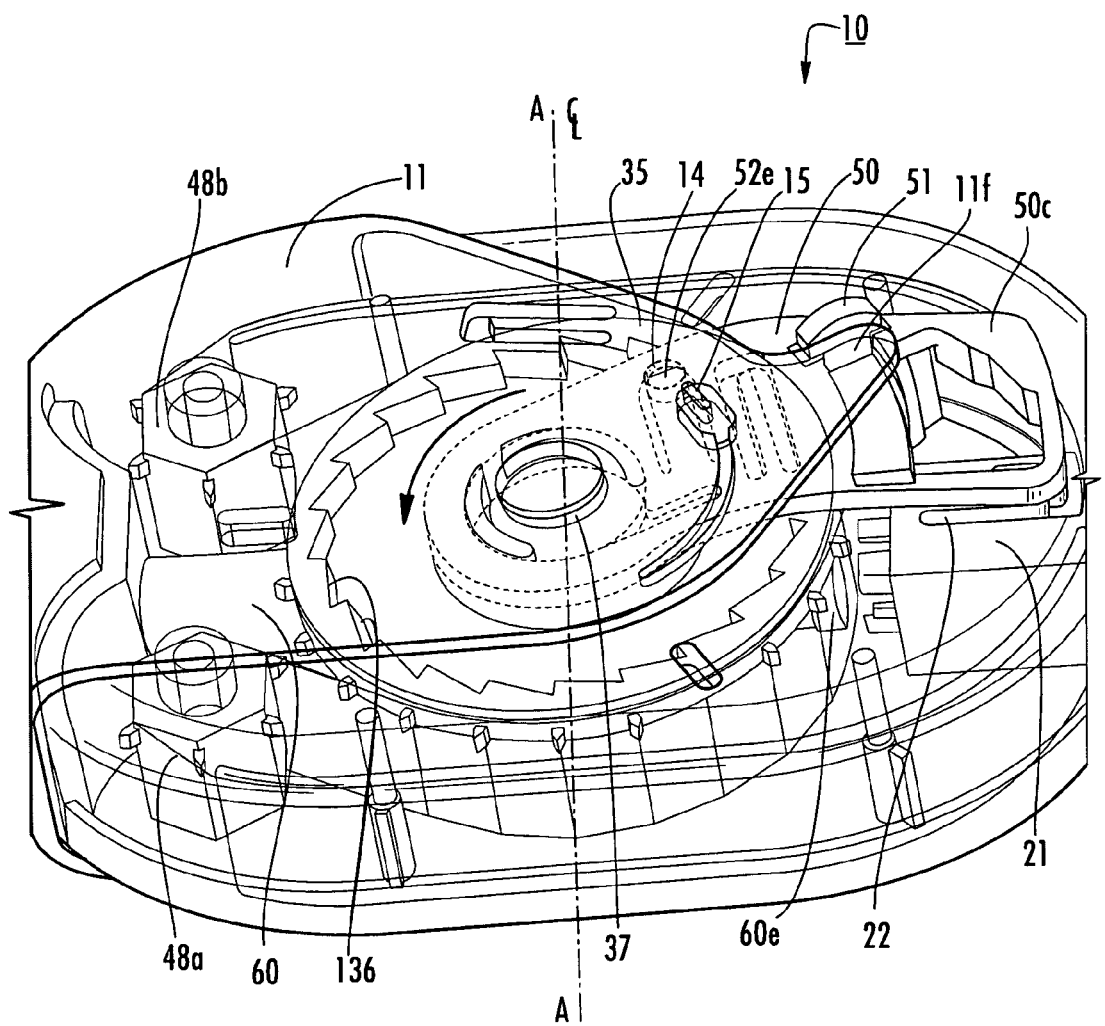

FIG. 9B shows the tongue 50 with the cam surface 50c in a side perspective view (with the inhaler cover and body shown partially transparent). FIG. 9B also shows that the tongue 50 can communicate with the cover 11 so that when the cover 11 is opened, the tongue 50 is allowed to move (e.g., rotate) to cause the piercer 20 to advance (and partially retract). In the embodiment shown, a lever 51 on the tongue 50 cooperates with a finger 11f on the cover 11. FIG. 9B also illustrates that the cover 11, tongue 50 and center member 35 can all have the same axis of rotation "A".

The cover 11 can communicate with an indexing mechanism to cause the center member 35 to rotate a defined distance to serially index a respective dose container 30d or blister 30b into the dispensing position 33 (FIG. 6). Typically, the indexing is counterclockwise (e.g., the center member 35 rotates ccw) as shown in FIG. 9B to move a "full" dose container/blister into position. The indexing can optionally be done upon closing or opening of the cover 11. In other embodiments, the indexing can be independent of the opening/closing of the cover, such as via a switch or lever actuation by a user (not shown).

Still referring to FIG. 9B, the center member 35 can include gear teeth 136 that cooperate with the center post 37 (optionally via a set of gears residing nested in the interior space of the center member that communicate with a center post 37 and gear teeth 136) such that the rotation of the cover 11 rotates the post 37, which, in turn, rotates the center member 35 one angular increment to place the next dose container/blister in the dispensing position X (FIG. 6).

Figure 11A:
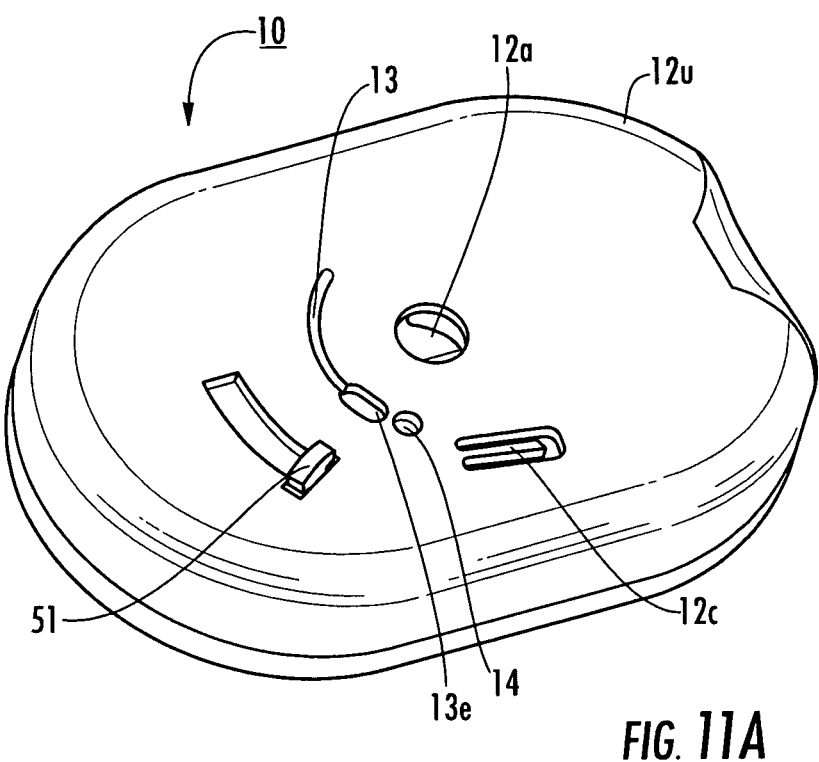
Figure 11B:
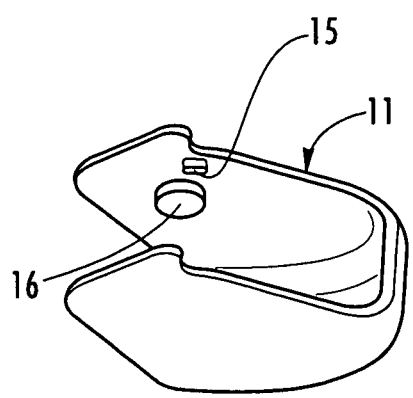

As will be discussed with respect to FIGS. 11A-11D, in particular embodiments, the cover 11, the upper inhaler housing 12u, and the tongue 50 cooperate to turn the center member 35 and index the strip 30, 30'. FIG. 11A illustrates the inhaler 10 without the cover 11 for ease of discussion. As shown, the upper inhaler housing 12u includes an aperture 12a that rotably receives a downwardly projecting member 16 of the cover 11 as shown in FIG. 11B. As is also shown, the upper housing 12u also includes a relatively narrow arcuate slot 13 that merges into a wider end portion 13e. The upper housing 12u can also include a substantially circular through-aperture 14 that resides adjacent the slot 13. In addition, the upper housing may include a cantilevered arm 12c.

Referring again to FIG. 11B, the cover 11 can also include a smaller downwardly extending projection 15 (shown as an obround projection) that travels in slot 13 of the inhaler housing 12u upon opening and closing of the cover 11.

Figure 11C:
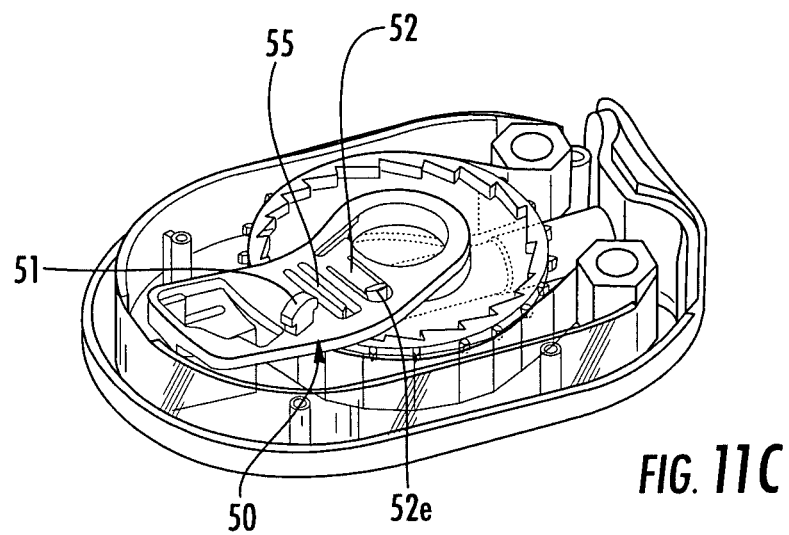
Figure 11D:
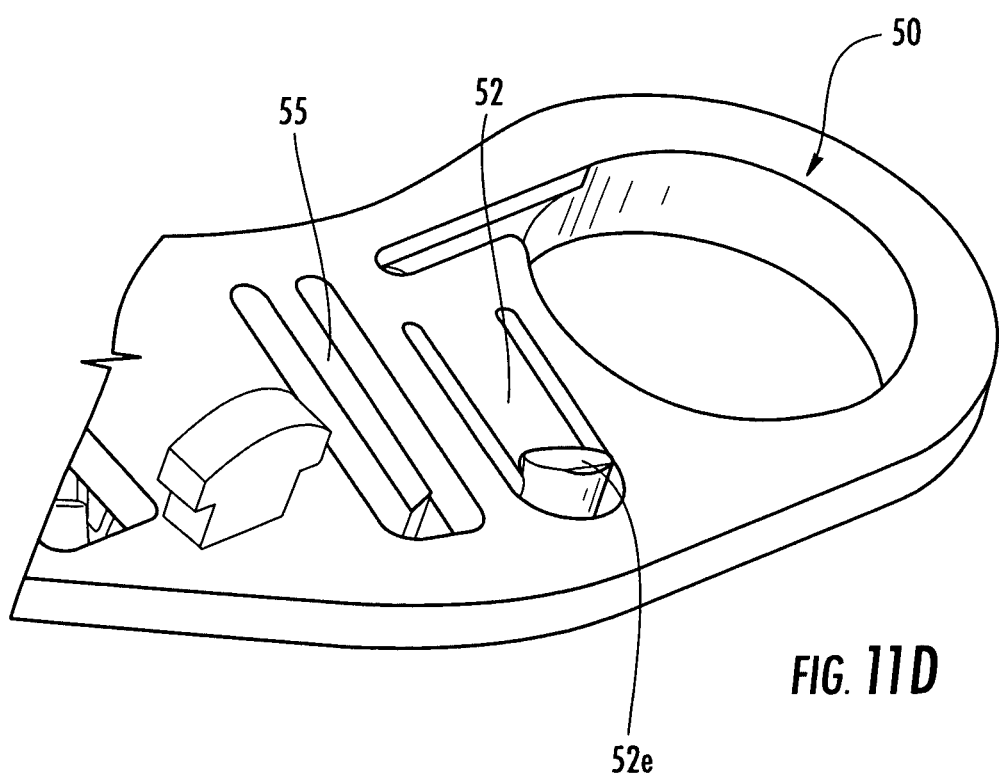

As discussed above, the tongue 50 is configured to partially retract the piercer 20 after piercing a blister/dose container in the dispensing position (33, FIG. 6) based on the position of the member 20u in the cut out surface 50c (FIGS. 9A, 9B). The tongue 50 may also be used to help index the strip 30, 30'. As shown in FIGS. 11C and 11D, in some embodiments, the tongue 50 can include two cantilevered arms 52, 55. One end portion of arm 52 includes an upwardly projecting ramped portion 52e. The ramped end portion 52e can be substantially circular (when viewed from the top) and can, in a certain orientation/position (see, e.g. FIG. 9B), reside in the circular aperture 14 of the inhaler housing 12u (FIGS. 1, 2, and 11A). As the cover 11 moves, the ramped end portion 52e can enter the wider end of the slot 13e. The cover projection 15 travels from the wider end of the slot 13e (FIG. 1) when the cover 11 is closed to closer to the opposing forward end of the slot 13 during piercing and delivery (inhalation) as shown in FIGS.

10A and 10B. FIG. 10C shows the cover projection 15 traveling from the position shown in FIG. 10B toward the position shown in FIG. 1.

FIG. 1 shows the inhaler 10 with the cover 11 closed and the projection 15 in position relative to the ramp portion 52e of the cantilevered arm 52. The cantilevered arm 55 engages the center member 35 during the (counterclockwise) closing of the cover 11 to drive the center member 35.

In some embodiments, the indexing occurs on the closing of the cover 11 and the return of the cantilevered arm 55 which can engage teeth 136 of the center member 35. FIG. 10A illustrates the position of the components discussed with respect to FIGS. 11A-11D during piercing and FIG. 10B shows them during subsequent inhalation/delivery. FIG. 10C shows the components as a return action of the cover causes a release action, e.g., as projection 15 moves into the wide end of the slot 13e which pushes the ramp portion 52e out of the slot 13e and down and the ramp portion 52e translates under the cover surface over to center aperture 14. The cantilevered arm 55 translates to engage the teeth 136 on the outer perimeter of the upper portion of the center member 35 and indexes the strip 30, 30'.

Figure 12:
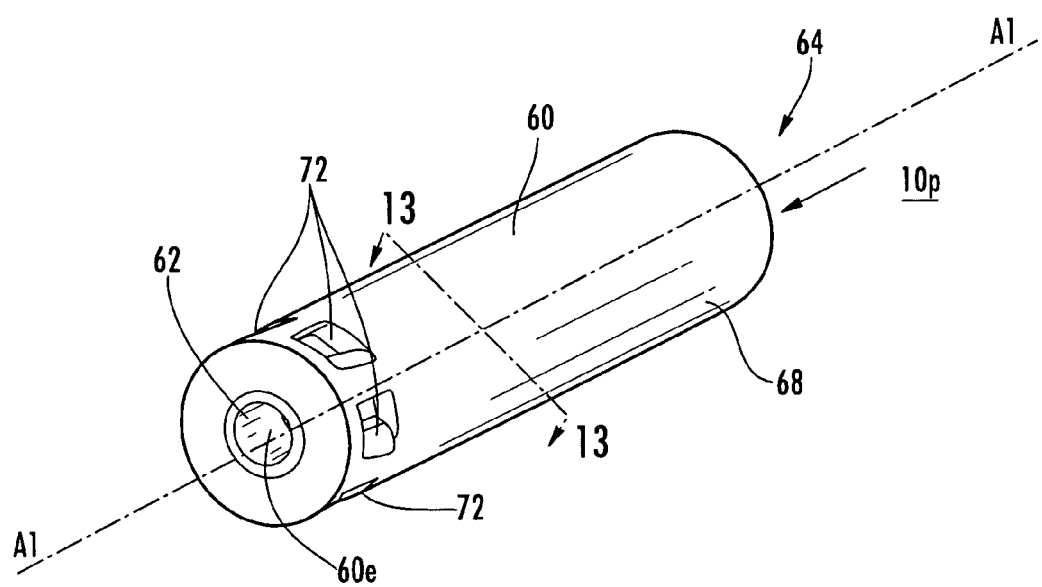

FIG. 12 illustrates an elongated dry powder delivery tube 60 for use with a dry powder inhaler 10 according to some embodiments of the present invention. The illustrated delivery tube 60 has an inlet 62 at one end 60e that is configured to communicate with a respective blister 30b or dose container 30d in the dispensing position (when opened) and an outlet 64 at an opposite end that is in communication with inhalation port 10p and/or mouthpiece 10m. The delivery tube has a wall 66 (FIG. 13) with an outer surface 68 and an inner surface 70. In the illustrated embodiment, the outer surface 68 of the delivery tube wall 66 has a substantially cylindrical configuration. However, embodiments of the present invention are not limited to a tube with a cylindrical configuration. Other delivery paths not employing tubes within an inhaler housing 12 can be utilized without limitation.

Figure 13:
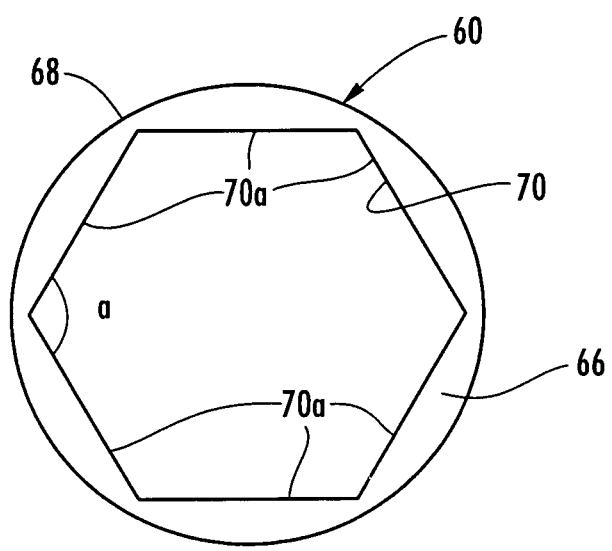
Figure 14:
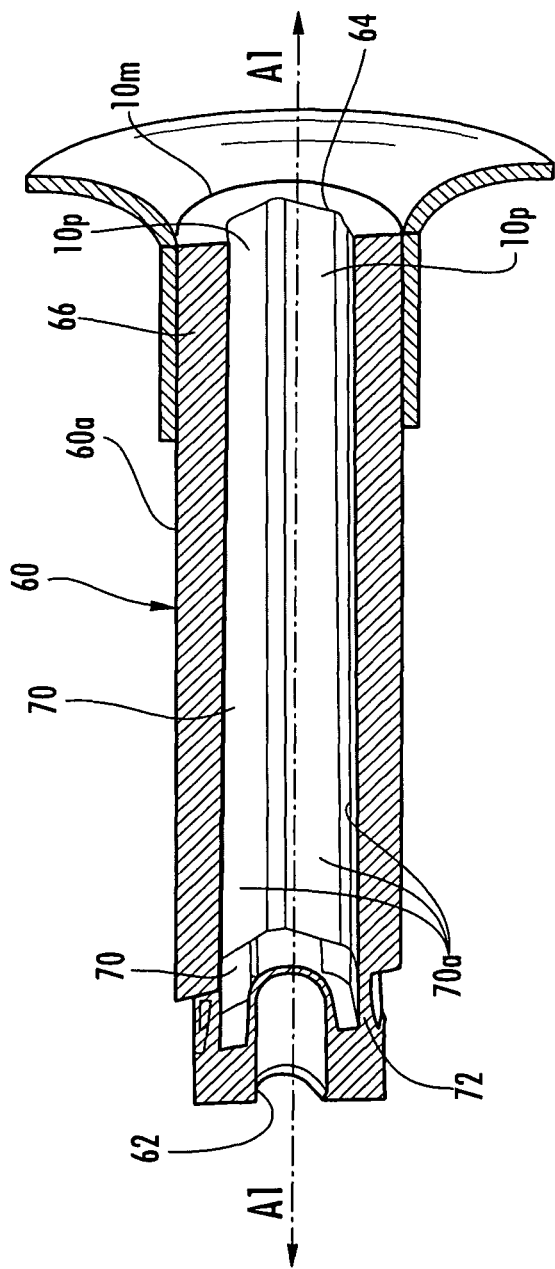
Figure 15:
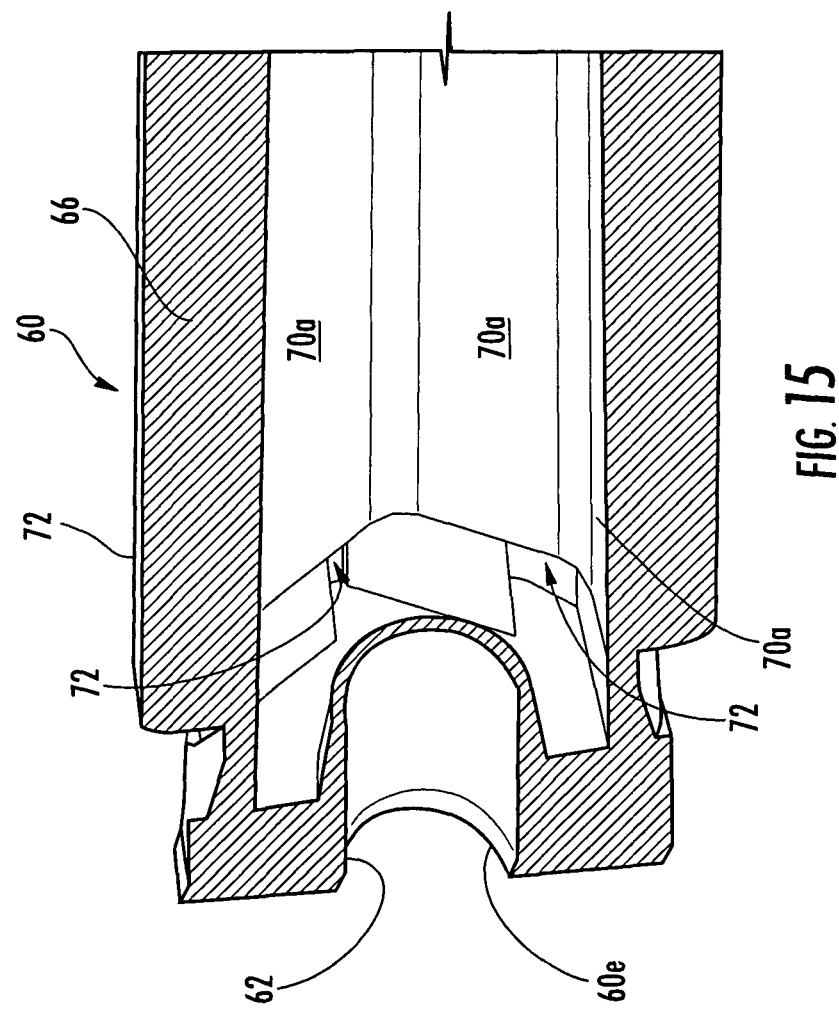

In the illustrated embodiment shown in FIGS. 13-15, for example, the delivery tube 60 has a substantially straight configuration without any changes of direction, but in other embodiments the tube 60 can have bends (not shown). The delivery tube wall 66 can include one or more apertures 72 adjacent the inlet 62 that provides airflow into the delivery tube 60 when a user inhales through the inhalation port 10p. This airflow can supplement airflow having/containing the dry powder medicament from a blister/dose container 30b, 30d in communication with the tube inlet 62 and the dry powder medicament becomes entrained within the air stream as would be understood by those skilled in the art of inhalers. In some embodiments, the apertures 72 are oriented such that airflow therethrough enters the tube 60 in a direction that is substantially transverse to a longitudinal axis $A_1$ of the tube such that the air stream impacts the tube wall inner surface 70.

In the illustrated embodiments of FIGS. 13 and 15, a plurality of circumferentially spaced-apart apertures 72 are provided about the dry powder intake end 60e. Apertures 72 can be configured as through channels or slots in the tube wall 66 that are oriented at acute radial angles to cause a turbulent or cyclonic air stream through the tube 60 when a user inhales through the inhalation port 10p. In some embodiments, the slots 72 can be substantially tangential to the tube wall inner surface 70. The turbulent or cyclonic air stream with entrained dry powder released from a dose container 30d or blister 30b repeatedly impacts the polygonal inner surface 70 of the delivery tube 60.

In some embodiments, small bleed holes can be provided through the tube wall 66 in one or more locations to prevent dry powder deposition and/or to facilitate airflow through the delivery tube 60 during inhalation by a user (not shown).

As shown in FIG. 13, at least a portion of the tube wall inner surface 70 has a multi-facet configuration, e.g., a polygonal cross-section configuration with a plurality of elongated planar surfaces 70a that are oriented substantially parallel with a longitudinal axis $A_1$ (FIG. 12) of the delivery tube 60. For example, as illustrated in FIG. 13, the tube wall inner surface can have a hexagonal configuration with six (6) planar surfaces 70a. In some embodiments, substantially the entire length of the tube wall inner surface 70 can have a polygonal configuration, as illustrated in FIG. 14. The polygonal cross-section can be less than the entire length, e.g., extend for about 20-70% of the length and/or transition to some other shape, for example at inlet 62 and/or outlet 64. In addition, the polygonal cross-section may flare out or have constant size along the distance/length of delivery tube 60.

The polygonal configuration of the tube wall inner surface 70 can cause the air stream to bounce off of each of the planar surfaces 70a (e.g., facets) numerous times as the air stream flows through the delivery tube 60. The multiple impacts combined with the shear forces imparted by the cyclonic air stream can facilitate deagglomeration of dry powder medicament entrained within the air stream. As such, the delivery tube 60 serves as an effective deagglomeration chamber for deagglomerating dry powder medicament being inhaled therethrough by a user.

In some embodiments, the impact surfaces 70a may have a finish that facilitates deagglomeration. For example, the impact surfaces 70a may have a substantially smooth, polished finish that facilitates accurate particle bounce angles, such as a Society of the Plastics Industry (SPI) rated finish SPI A2. In other embodiments, the impact surfaces 70a may have a substantially rough or matte finish that facilitates particle spin, such as an SPI B3 finish.

Air inlet apertures 72 can have various configurations for generating cyclonic air streams, and embodiments of the present invention are not limited to the illustrated number or configuration of apertures 72. In addition, embodiments of the present invention are not limited to tube wall inner surfaces with hexagonal configurations. Various polygonal configurations are possible for the inner wall/surface 70 including, but not limited to, heptagonal, octagonal, nonagonal, decagonal, etc. . . . Angles between adjacent elongated planar surfaces 70a can be, for example, greater than or equal to about one-hundred five degrees (105°), greater than or equal to about one-hundred twenty degrees (120°), greater than or equal to about one-hundred thirty-five degrees (135°), etc.

In the illustrated embodiment, the delivery tube inlet 62 is smaller than the delivery tube outlet 64. For example, a cross-sectional area of the tube inlet 62 can be less than or equal to a cross-sectional area of the tube outlet 64. An air stream flowing though the delivery tube 60 creates a low pressure core that helps pull air through a dose container to remove powder therefrom. In addition, Applicants have discovered that a delivery tube outlet 64 that is larger than the delivery tube inlet 62 may also facilitate evacuation of dry powder medicament from blisters 30b and/or dose containers 30d.

Figure 16:
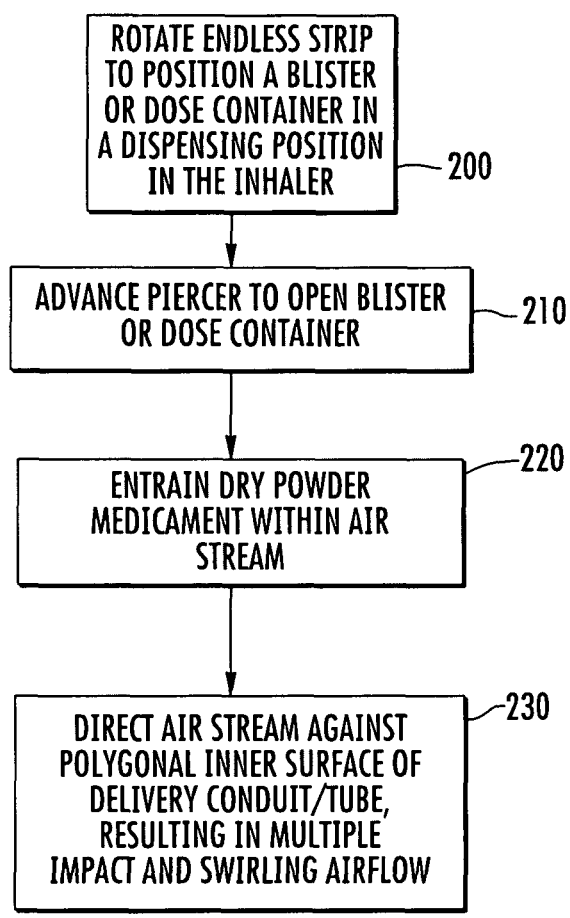

FIG. 16 illustrates exemplary operations for dispensing dry powder medicament from a dry powder inhaler 10 according to some embodiments of the present invention. The operations include rotating an endless blister strip inside a dry powder inhaler (block 200) to serially place a respective blister in a dispensing position. Advancing a piercer to open the blister (block 210). Dry powder medicament from the opened blister is entrained within an air stream (block 220), for example, by a user inhaling through inhalation port 10p of inhaler 10. The air stream may be a cyclonic or otherwise turbulent air stream. The air stream with dry powder entrained therein may optionally be directed against a polygonal inner surface of a delivery conduit/tube, resulting in multiple impacts and swirling airflow (block 230). This optional step may facilitate deagglomeration of the dry powder without causing the dry powder to lose velocity and accumulate within the inhaler.

The inhaler embodiments described herein may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl) ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler described herein include medicaments that are selected from the group consisting of: albuterol, salmeterol, fluticasone propionate and beclometasone dipropionate and salts or solvates thereof, e.g., the sulphate of albuterol and the xinafoate of salmeterol.

Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A dry powder inhaler, comprising:
   an inhaler body defining an inner cavity, the inhaler body having a mouthpiece;
   an endless strip having opposing primary surfaces held in the inhaler body cavity, the strip comprising a plurality of spaced apart blisters and/or dose containers holding dry powder medicament;
   an inhalation exit flow path in the inhaler body that extends in an axial direction and merges into the mouthpiece, the inhalation exit flow path in communication with at least one blister or at least one dose container, respectively, in a dispensing position;
   a piercer in the inhaler body, the piercer configured to extend in the axial direction in line with the inhalation flow path to open the blister or dose container in the dispensing position; and
   a plurality of guide members spaced apart about the inhaler cavity that cooperably engage the strip and hold the strip in a shape that has only a single curvilinear inner portion that merges into only a single curvilinear outer portion while allowing the strip to rotate in the inner cavity to position blisters and/or dose containers to the dispensing position,
   wherein the piercer is positioned in the inhaler body cavity spaced apart from and opposing the mouthpiece with an enclosed member providing the inhalation exit flow path therebetween, and wherein the piercer is configured to radially translate a distance sufficient to fully pierce the blister or dose container in the dispensing position, then partially retract a distance sufficient to reside in a position to occlude a pierced opening in the blister or dose container during a dispensing operation.

2. The dry powder inhaler of claim 1, wherein the guide members include a plurality of spaced apart rotatable posts, one positioned proximate the mouthpiece on each side of the inhalation exit flow path in the inhaler body, at least one stationary outer guide member residing proximate an outer wall of the inhaler body and at least one inner guide member residing transversely spaced apart from at least one outer guide member, wherein the posts and the inner and outer guide members cooperate to hold the strip in the cavity of the inhaler body with the primary surfaces of the strip oriented in a substantially vertical orientation such that the strip has a constant perimeter shape and translates to present respective blisters or dose containers into the dispensing position, and wherein the inner guidewall includes left and right segments with opposing ends, an innermost end facing the mouthpiece and an outermost end residing further away from the mouthpiece, left and right outermost ends of respective left and right segments have an open space extending therebetween, and wherein the piercer is configured to extend to pierce a dose container or blister positioned across the open space between the right and left outermost ends.

3. The dry powder inhaler of claim 1, wherein the guide members include an inner guidewall disposed in the inhaler body cavity, an outer guidewall disposed in the inhaler body cavity spaced apart from the inner guidewall and residing proximate an outer wall of the inhaler body, and a pair of spaced apart rotatable posts in the inhaler body cavity residing proximate the mouthpiece one on each side of the inhalation exit flow path, wherein the piercer resides in the inhaler body aligned with and opposing the mouthpiece between the inner and outer guidewalls, and wherein the inner guidewall, the outer guidewall and the posts concurrently engage the strip while allowing the strip to translate to present the respective blisters and/or dose containers in the dispensing position.

4. The dry powder inhaler of claim 3, further comprising a rotating member with a plurality of outwardly extending tabs residing above or under the inner guidewall that extend through apertures in the strip to engage the strip and rotate the respective blisters or dose containers into the dispensing position.

5. The dry powder inhaler of claim 4, wherein the dispensing position is aligned with an open space of the outer guidewall and the strip contacts an outer surface of the outer guidewall and extends over the open space thereof, and wherein the piercer is configured to radially translate outward either (a) toward the outer guidewall or (b) toward the inner guidewall, aligned with the open space of the outer guidewall to pierce the blister or dose container in the dispensing position and release the dry powder medicament into the exit flow path.

6. The dry powder inhaler of claim 4, wherein the rotating member is circular, and wherein the rotating member includes circumferentially spaced apart outwardly projecting tabs that communicate with apertures on the strip and wherein the rotating member and the rotating posts cooperate with respective tabs to incrementally rotate the strip to serially place respective blisters or dose containers into the dispensing position.

7. The dry powder inhaler of claim 1, wherein the guide members include a plurality of rotatable posts that have a respective upwardly extending polygonal wall, each facet of the polygonal wall having a width sufficient to hold one blister or dose container thereagainst, and wherein the posts have outwardly projecting tabs that reside on an outer corner of each facet of the polygonal wall and communicate with the strip.

8. The dry powder inhaler of claim 1, wherein the strip is a flexible strip and is held in the inhaler body to have a constant perimeter shape with the single curvilinear outer portion being an obround outer portion and with the single curvilinear inner portion spaced apart from the single obround outer portion.

9. The dry powder inhaler of claim 1, wherein the strip is a blister strip, and wherein one of the guide members is a stationary inner guidewall with upwardly extending sidewalls, the sidewalls having an outer surface with a plurality of adjacent spaced apart recesses, each recess configured to abut and hold a protrusion associated with a respective blister.

10. The dry powder inhaler of claim 7, wherein the strip has longitudinally spaced apart apertures that communicate with tabs on the posts, and wherein each blister or dose container is held by a strip segment with bendable edges to allow the posts to snugly hold a respective segment substantially flat against a corresponding one of the plurality of the facets of the posts.

11. The dry powder inhaler of claim 1, wherein the exit airflow path comprises a tubular conduit having a wall with an inner surface with a polygonal cross-section, wherein dry powder is drawn from the tubular member to the mouthpiece upon user inhalation.

12. The dry powder inhaler of claim 11, wherein the polygonal inner surface comprises a plurality of elongated planar surfaces with an angle between adjacent elongated planar surfaces being greater than or equal to about one-hundred five degrees) (105°, optionally greater than or equal to about one-hundred twenty degrees)(120° or optionally greater than or equal to about one-hundred thirty-five degrees (135°).

13. The dry powder inhaler of claim 11, wherein the tubular conduit has an end portion that comprises circumferentially spaced apart air inlet apertures that are in fluid communication with the exit air flow path through an interior channel of the tubular conduit.

14. The inhaler of claim 1, wherein the inhaler body has an upper housing with an outer surface with an arcuate slot and an adjacent spaced apart circular aperture extending therethrough, the inhaler further comprising a tongue with a cantilevered arm having a ramped end portion residing under the upper housing and a cover residing over the upper housing and being rotably mounted thereto, the cover having a downwardly projecting member that travels in the slot whereby as the cover moves between open and closed positions or closed and open positions, the ramped end portion of the cantilevered arm is configured to serially enter the arcuate slot and the circular aperture.

15. A dry powder inhaler, comprising:
an inhaler body defining an inner cavity, the inhaler body having a mouthpiece;
an endless strip having opposing primary surfaces held in the inhaler body cavity, the strip comprising a plurality of spaced apart blisters and/or dose containers holding dry powder medicament;
an inhalation exit flow path in the inhaler body that extends in an axial direction and merges into the mouthpiece, the inhalation exit flow path in communication with at least one blister or at least one dose container, respectively, in a dispensing position;
a piercer in the inhaler body, the piercer configured to extend in the axial direction in line with the inhalation flow path to open the blister or dose container in the dispensing position;
a plurality of guide members spaced apart about the inhaler cavity that cooperably engage the strip and hold the strip in a shape that has only a single curvilinear inner portion that merges into only a single curvilinear outer portion while allowing the strip to rotate in the inner cavity to position blisters and/or dose containers to the dispensing position, wherein the guide members include an inner guidewall disposed in the inhaler body cavity, an outer guidewall disposed in the inhaler body cavity spaced apart from the inner guidewall and residing proximate an outer wall of the inhaler body, and a pair of spaced apart rotatable posts in the inhaler body cavity residing proximate the mouthpiece one on each side of the inhalation exit flow path, wherein the piercer resides in the inhaler body aligned with and opposing the mouthpiece between the inner and outer guidewalls and wherein the inner guidewall, the outer guidewall and the posts concurrently engage the strip while allowing the strip to translate to present the respective blisters and/or dose containers in the dispensing position; and
a rotating member with a plurality of outwardly extending tabs residing above or under the inner guidewall that extend through apertures in the strip to engage the strip and rotate the respective blisters or dose containers into the dispensing position,
wherein the dispensing position is aligned with an open space of the inner guidewall, residing proximate a tube extending inward from the mouthpiece across a medial portion of the inhaler body cavity, and the strip contacts an outer surface of the inner guidewall and extends over the open space, and wherein the piercer resides at a position in the inhaler body opposing the mouthpiece proximate an inner end of the tube and is configured to radially advance to pierce the blister or dose container in the dispensing position and release the dry powder medicament into the exit flow path.

16. A dry powder inhaler, comprising:
an inhaler body defining an inner cavity;

an endless strip having opposing primary surfaces held in the inhaler body cavity, the strip comprising a plurality of spaced apart blisters and/or dose containers holding dry powder medicament;

an inhalation exit flow path in the inhaler body in communication with at least one blister or at least one dose container, respectively, in a dispensing position;

a piercer in the inhaler body, the piercer configured to open the blister or dose container in the dispensing position;

a plurality of guide members spaced apart about the inhaler cavity that cooperably engage the strip and hold the strip in a shape that has a semi-circular inner portion that merges into a curvilinear outer portion while allowing the strip to rotate in the inner cavity to position blisters and/or dose containers to the dispensing position, wherein the guide members include an inner guidewall disposed in the inhaler body cavity, an outer guidewall disposed in the inhaler body cavity spaced apart from the inner guidewall and residing proximate an outer wall of the inhaler body, and a pair of spaced apart rotatable posts in the inhaler body cavity, the inner guidewall, the outer guidewall and the posts concurrently engage the strip while allowing the strip to translate to present the respective blisters and/or dose containers in the dispensing position, wherein the inner guidewall has a pair of spaced apart upwardly extending semi-circular portions with open segments between each end of the semi-circular portions with one open segment defining at least one open space aligned with the piercer, and wherein the piercer radially reciprocates in a direction that is substantially orthogonal to the primary surfaces of the strip in the dispensing position; and a tubular conduit having first and second opposing end portions, the tubular conduit residing between the semi-circular portions of the inner guidewall with the first end portion in fluid communication with a mouthpiece in fluid communication with the inhalation exit flow path and the second end portion facing and aligned with the piercer, and with one of the rotatable posts on each side of the first end portion of the tubular conduit.

17. A dry powder inhaler, comprising:
an inhaler body defining an inner cavity;
an endless strip having opposing primary surfaces held in the inhaler body cavity, the strip comprising a plurality of spaced apart blisters and/or dose containers holding dry powder medicament;
an inhalation exit flow path in the inhaler body in communication with at least one blister or at least one dose container, respectively, in a dispensing position;
a piercer in the inhaler body, the piercer configured to open the blister or dose container in the dispensing position; and
a plurality of guide members spaced apart about the inhaler cavity that cooperably engage the strip and hold the strip in a shape that has a semi-circular inner portion that merges into a curvilinear outer portion while allowing the strip to rotate in the inner cavity to position blisters and/or dose containers to the dispensing position,
wherein the piercer has a sharp tip that extends horizontally outward toward a mouthpiece held by the inhaler body in fluid communication with the exit flow path, and wherein the piercer has an upwardly extending sliding member that resides in a holder with a radially extending slot, the upwardly extending sliding member configured to travel back and forth in the slot causing the piercer tip to travel radially back and forth during operative use, and wherein the sliding member communicates with a rotating tongue with a cam surface held by the inhaler body whereby the sliding member is directed to radially translate back and forth in the slot based on contact with different portions of the cam surface.

18. The dry powder inhaler of claim 17, wherein the guide members includes a stationary inner guide wall that supports a rotating circular center member about an axis of rotation, and wherein the tongue resides above the center member and has an axis of rotation that is coincident with that of the rotating center member, and wherein the center member and the tongue are in communication with a rotating cover that resides over an outer surface of the inhaler body and has a center of rotation that is coincident with the rotating center member and tongue whereby opening or closing of the cover causes the center member to rotate which (a) rotates a blister or dose container on the strip to a dispensing position and (b) allows the upwardly extending member of the piercer in the slot of the holder to retract.

19. A dry powder inhaler, comprising:
an inhaler body defining an inner cavity, the inhaler body having a mouthpiece;
an endless strip having opposing primary surfaces held in the inhaler body cavity, the strip comprising a plurality of spaced apart blisters and/or dose containers holding dry powder medicament;
an inhalation exit flow path in the inhaler body that extends in an axial direction and merges into the mouthpiece, the inhalation exit flow path in communication with at least one blister or at least one dose container, respectively, in a dispensing position;
a piercer in the inhaler body, the piercer configured to extend in the axial direction in line with the inhalation flow path to open the blister or dose container in the dispensing position; and
a plurality of guide members spaced apart about the inhaler cavity that cooperably engage the strip and hold the strip in a shape that has only a single curvilinear inner portion that merges into only a single curvilinear outer portion while allowing the strip to rotate in the inner cavity to position blisters and/or dose containers to the dispensing position,
wherein the endless strip is a first endless blister strip, the inhaler further comprising:
a second endless blister strip having opposing primary surfaces, the second strip comprising a plurality of spaced apart blisters holding dry powder medicament, wherein the second strip is held in the inhaler body cavity adjacent the first endless strip whereby the first and second strips rotate in concert to present respective blisters or dose containers in the dispensing position, wherein the second endless strip is held by the plurality of guide members that cooperably engage the first endless strip, and wherein the first and second endless strips are both held in the same shape to each have only a single curvilinear inner portion that merges into only a single curvilinear outer portion while allowing the strips to rotate in the inner cavity to position blisters and/or dose containers from the first and second strips to the dispensing position, and wherein the outer curvilinear portion of the first and second endless strips are parallel to each other and extend about both sides and across a rear segment of the inhaler body cavity.

20. A method operating an inhaler, comprising:
translating an endless strip of blisters or dose containers having a fixed perimeter shape with only two segments, a single obround outer segment that merges to a single inner curvilinear segment to both serially position respective dose containers or blisters in a defined dispensing position in the inhaler and move empty dose containers or blisters away from the dispensing position, wherein the endless strip has a constant perimeter shape with the single oblong outer segment merging to the single curvilinear inner segment at rotatable posts residing proximate the mouthpiece, a first post residing on one side of the inhalation exit flow path and a second rotatable post residing on an opposing side of the inhalation exit flow path whereby opposing legs of the curvilinear inner segment extend away from the mouthpiece toward an outer perimeter of the inhaler and define an opening in a center region in the inhaler;

rotating at least one member having outwardly extending tabs that engage the strip to carry out the translating step;

translating a piercer toward a dose container or blister in the dispensing position to open and release dry powder medicament therefrom; and capturing the released medicament in an exit flow path, wherein the piercer is positioned opposing a mouthpiece of the inhaler in fluid communication with a tubular member that extends between an open space defined between legs of the single inner curvilinear segment and the mouthpiece, wherein the translating the piercer step comprises radially translating between three positions during a piercing step, a home retracted first position, a radially translated first forwardmost position, and a third partially radially retracted position, the method further comprising, blocking an opening in the blister/dose container or a ort associated with an exit airflow path when the piercer is in the third position.

* * * * *

UNITED STATES PATENT AND TRADEMARK OFFICE
CERTIFICATE OF CORRECTION

PATENT NO. : 8,991,391 B2
APPLICATION NO. : 13/063511
DATED : March 31, 2015
INVENTOR(S) : McGee Perkins et al.

It is certified that error appears in the above-identified patent and that said Letters Patent is hereby corrected as shown below:

In the Claims:
Column 19, Claim 12, Lines 57 and 58: Please correct "(105°, optionally greater than or equal to about one-hundred twenty degrees)(120°"
    to read -- (105°), optionally greater than or equal to about one-hundred twenty degrees (120°) --

Column 21, Claim 16, Line 21: Please correct "cavity, the inner"
    to read -- cavity, wherein the inner --

Column 23, Claim 20, Line 25: Please correct "translating between"
    to read -- translating the piercer between --

Column 23, Claim 20, Line 30: Please correct "or a ort associated"
    to read -- or a port associated --

Signed and Sealed this
Fifth Day of January, 2016

Michelle K. Lee
*Director of the United States Patent and Trademark Office*